(12) United States Patent  (10) Patent No.: US 8,678,587 B2
Alpins  (45) Date of Patent: Mar. 25, 2014

(54) ASSESSMENT OF TOPOGRAPHIC SEMI-MERIDIAN PARAMETERS FOR CORNEAL ASTIGMATISM ANALYSIS AND VECTOR PLANNING TREATMENT

(76) Inventor: Noel Ami Alpins, Cheltenham (AU)

( * ) Notice: Subject to any disclaimer, the term of this patent is extended or adjusted under 35 U.S.C. 154(b) by 371 days.

(21) Appl. No.: 12/945,764

(22) Filed: Nov. 12, 2010

(65) Prior Publication Data

US 2011/0149240 A1  Jun. 23, 2011

Related U.S. Application Data

(60) Provisional application No. 61/260,556, filed on Nov. 12, 2009.

(51) Int. Cl.
*A61B 3/10* (2006.01)
*A61B 3/14* (2006.01)
*A61B 3/00* (2006.01)

(52) U.S. Cl.
USPC ............ 351/205; 351/210; 351/221; 351/246

(58) Field of Classification Search
USPC .......... 351/205–206, 210, 221–222, 246, 239
See application file for complete search history.

(56) References Cited

U.S. PATENT DOCUMENTS

| | | |
|---|---|---|
| 6,467,906 B1 | 10/2002 | Alpins |
| 2001/0055095 A1* | 12/2001 | D'Souza et al. ............. 351/212 |
| 2002/0103479 A1 | 8/2002 | Sarver |

FOREIGN PATENT DOCUMENTS

| | | |
|---|---|---|
| EP | 0 836 459 B1 | 7/2009 |
| WO | 98/17168 A2 | 4/1998 |

* cited by examiner

*Primary Examiner* — Dawayne A Pinkney
(74) *Attorney, Agent, or Firm* — Ladas & Parry LLP

(57) ABSTRACT

Techniques are disclosed in which a topographic parameter is determined in each semi-meridian of the eye by considering the topography in each of three concentric zones from the central axis at 3 mm, 5 mm, and 7 mm and assigning weighting factors for each zone, By selectively treating the weighted values in the three zones, parameters of magnitude and meridian can be obtained for each semi-meridian. From these parameters, a single topographic value for the entire eye (CorT) can be found as well as a value representing topographic disparity (TD) between the two semi-meridians. The topography values for the semi-meridians are used in a vector planning system to obtain treatment parameters in a single step operation.

17 Claims, 24 Drawing Sheets

Simulated K Values
42.00D (8.04 mm) @102
41.12D (8.21 mm) @12
Astigmatism: 0.88D
Overall
42.48D (7.94 mm) @290
41.84D (8.07 mm) @90
41.14D (8.20 mm) @24
41.22D (8.19 mm) @158
0-3 mm
41.54D (8.12 mm) @294
41.23D (8.19 mm) @90
40.46D (8.34 mm) @30
40.68D (8.30 mm) @164
3-5 mm
42.45D (7.95 mm) @276
41.87D (8.06 mm) @100
41.13D (8.21 mm) @12
41.17D (8.20 mm) @152
5-7 mm
44.04D (7.66 mm) @260
43.24D (7.81 mm) @66
42.18D (8.00 mm) @4
42.30D (7.98 mm) @158
OD

F I G. 1

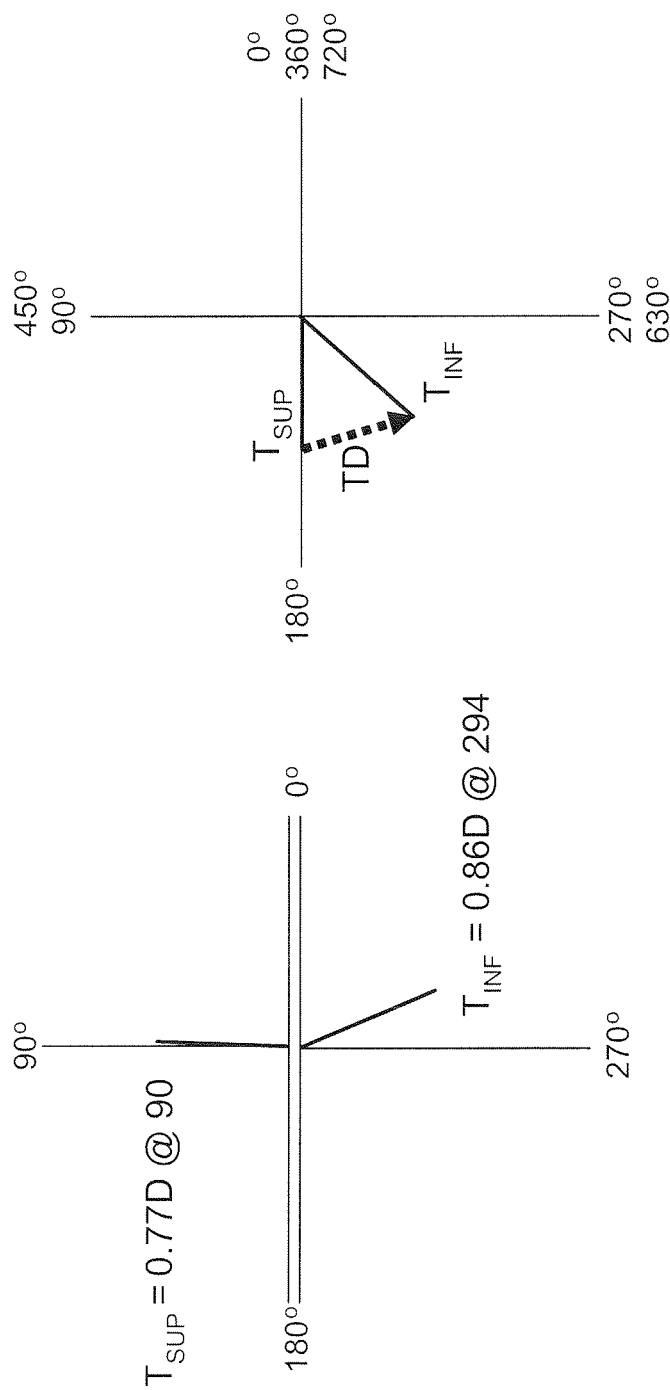

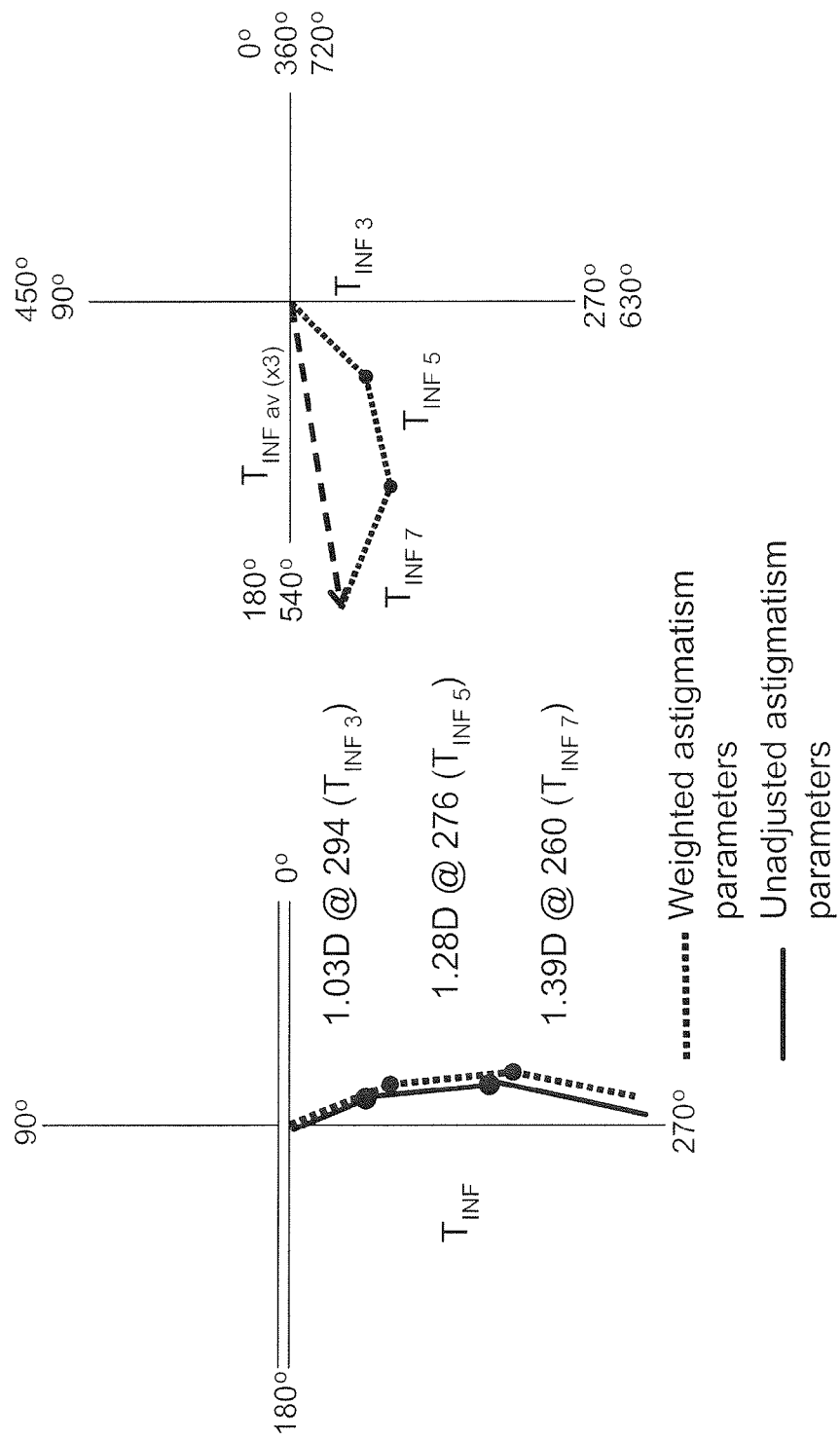

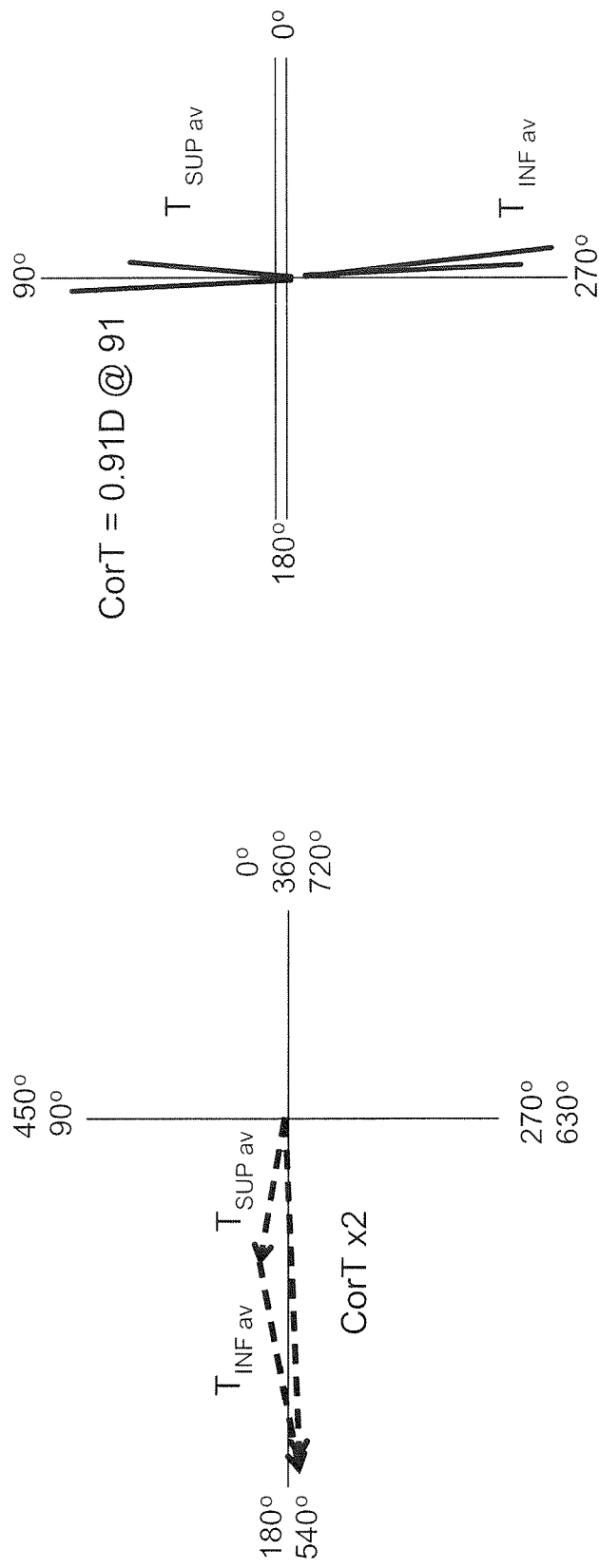

| Zones (mm) Superior | Unadjusted astigmatism (D) | Weighted astigmatism (D) |
|---|---|---|
| 3.0 | 0.77 @ 90 | 0.92 @ 90 |
| 5.0 | 0.74 @ 100 | 0.74 @ 100 |
| 7.0 | 1.06 @ 66 | 0.85 @ 66 |
| $T_{SUP\,av}$ | 0.75 @ 83 | 0.74 @ 85 |
| Zones (mm) Inferior | Unadjusted astigmatism (D) | Weighted astigmatism (D) |
| 3.0 | 0.86 @ 294 | 1.03 @ 294 |
| 5.0 | 1.28 @ 276 | 1.28 @ 276 |
| 7.0 | 1.74 @ 260 | 1.39 @ 260 |
| $T_{INF\,av}$ | 1.16 @ 272 | 1.10 @ 275 |

FIG. 6c

| Cornea(total) | Unadjusted astigmatism (D) | Weighted astigmatism (D) |
|---|---|---|
| TD | 0.50 Ax 106 | 0.48 Ax 111 |
| CorT | 0.95 @ 88 | 0.91 @ 91 |
| Sim K | 0.88 @ 102 | |
| Astigmatism mean (arithmetic) (3, 5, 7mm zones) | 1.08 | 1.04 |

FIG. 6d

| SUPERIOR SEMI-MERIDIAN (all values at corneal plane) | Topography (D) | Plus Cylinder Refraction (DC) | Minus Cylinder Refraction (DC) |
|---|---|---|---|
| Preop | 2.60 @ 130 | +1.63 Ax 108 | -1.63 Ax 18 |
| TIA $_{SUP\ AB}$ | 1.87 Ax 29 | | |

| INFERIOR SEMI-MERIDIAN (all values at corneal plane) | Topography (D) | Plus Cylinder Refraction (DC) | Minus Cylinder Refraction (DC) |
|---|---|---|---|
| Preop | 1.90 @ 278 | +1.63 Ax 288 | -1.63 Ax 198 |
| TIA $_{INF\ AB}$ | 1.71 Ax 194 | | |

| SUPERIOR SEMI-MERIDIAN (AB) | Topography (D) |
|---|---|
| Preop | 2.60 @ 130 |
| TIA $_{SUP\ AB}$ | 1.87 Ax 29 |
| Target T $_{SUP\ B}$ | 1.09 @ 149 |

| INFERIOR SEMI-MERIDIAN (AB) | Topography (D) |
|---|---|
| Preop | 1.90 @ 278 |
| TIA $_{INF\ AB}$ | 1.71 Ax 194 |
| Target T $_{INF\ B}$ | 0.40 @ 250 |

| SUPERIOR SEMI-MERIDIAN (AB) | Wavefront Refraction (DC) |
|---|---|
| Preop | 1.63 Ax 108 |
| TIA $_{SUP\ AB}$ | 1.87 Ax 29 |
| Target R $_{SUP\ B}$ | 0.73 Ax 59 |

| INFERIOR SEMI-MERIDIAN (AB) | Wavefront Refraction (DC) |
|---|---|
| Preop | 1.63 Ax 288 |
| TIA $_{INF\ AB}$ | 1.71 Ax 194 |
| Target R $_{INF\ B}$ | 0.27 Ax 340 |

$TIA_{NET\ AB\ x1}\ (1.73\ Ax\ 22) = [TIA_{SUP\ AB}\ (1.87\ Ax\ 29) + TIA_{INF\ AB}\ (1.71\ Ax\ 194)] \times 1/2$

| Calculation of Target $R_B$ (AB) | Plus Cylinder Refraction (DC) | Minus Cylinder Refraction (DC) |
|---|---|---|
| Preop | +1.63 Ax 108 | -1.63 Ax 18 |
| $TIA_{NET\ AB}$ | 1.73 Ax 22 | |
| Target $R_B$ | +0.25 Ax 53 | -0.25 Ax 143 |

| SUPERIOR SEMI-MERIDIAN (BC) | Topography (D) |
|---|---|
| Preop | 1.09 @ 149 |
| TIA $_{SUP\ BC}$ | 1.34 Ax 58 |
| Target T $_{SUP\ C}$ | 0.25 @ 53 |

| INFERIOR SEMI-MERIDIAN (BC) | Topography (D) |
|---|---|
| Preop | 0.40 @ 250 |
| TIA $_{INF\ BC}$ | 0.24 Ax 357 |
| Target T $_{INF\ C}$ | 0.25 @ 233 |

| SUPERIOR SEMI-MERIDIAN (BC) | Wavefront Refraction (DC) |
|---|---|
| Preop | 0.25 Ax 53 |
| TIA $_{SUP\ BC}$ | 1.34 Ax 58 |
| Target R $_{SUP\ C}$ | 1.59 Ax 57 |

| INFERIOR SEMI-MERIDIAN (BC) | Wavefront Refraction (DC) |
|---|---|
| Preop | 0.25 Ax 233 |
| TIA $_{INF\ BC}$ | 0.24 Ax 357 |
| Target R $_{INF\ C}$ | 0.27 Ax 206 |

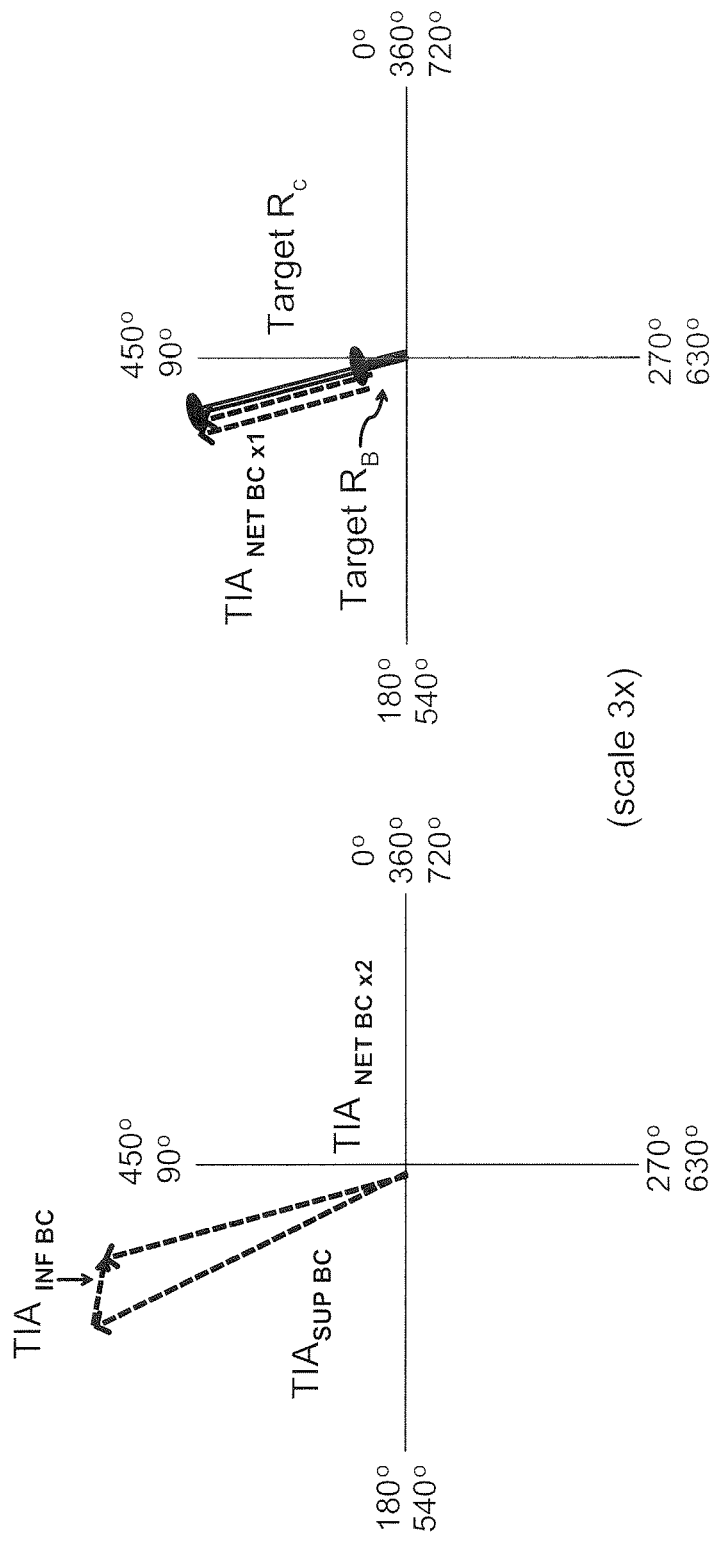

| SUPERIOR SEMI-MERIDIAN (AC) | Topography (D) |
|---|---|
| Preop | 2.60 @ 130 |
| TIA $_{SUP\,AC}$ | 2.84 Ax 41 |
| Target T $_{SUP\,C}$ | 0.25 @ 53 |

| INFERIOR SEMI-MERIDIAN (AC) | Topography (D) |
|---|---|
| Preop | 0.90 @ 278 |
| TIA $_{INF\,AC}$ | 0.92 Ax 191 |
| Target T $_{INF\,C}$ | 0.25 @ 53 |

US 8,678,587 B2

ASSESSMENT OF TOPOGRAPHIC SEMI-MERIDIAN PARAMETERS FOR CORNEAL ASTIGMATISM ANALYSIS AND VECTOR PLANNING TREATMENT

CROSS-REFERENCES TO RELATED APPLICATIONS

This application claims the benefit of U.S. Provisional Application No. 61/260,556 filed on Nov. 12, 2009, which is incorporated herein by reference.

FIELD OF THE INVENTION

The invention relates to the determination of astigmatism parameters to represent each semi-meridian of the cornea derived from the keratometric view of topography for use in vector analysis and planning of treatment. These two semi-meridian values (for the superior and inferior semi-meridians) can then together determine a single corneal topography value for magnitude and meridian as an alternative to simulated keratometry as well as quantifying the irregularity of the cornea.

The invention further relates to a vector planning modality to simultaneously reduce and regularize naturally occurring irregular corneal astigmatism achieved by applying different laser ablation profiles to each of the two semi-meridians of the cornea. This treatment plan combines both topographic and refractive (wavefront) parameters and can be used as an algorithm for excimer laser technology applications to reduce ocular aberrations and improve visual performance.

SUMMARY OF THE INVENTION

According to the invention, a keratometric map is obtained by computer assisted videokeratography and vector summation is employed to determine two semi-meridian parameters to quantify astigmatism for the separate halves of the cornea. These astigmatism magnitudes can be weighted for 3 mm, 5 mm and 7 mm concentric zones subscribed from the central axis of the cornea so that corneal astigmatism and irregularity can then be quantified. Namely, there are two factors which influence the weighting to be assigned to the 3 mm, 5 mm and 7 mm zones. These are 1) proximity to the central axis of the cornea and 2) the area subscribed by the respective zones. Based on these factors I have found that suitable theoretical weighting coefficients for the 3 mm zone is 1.2, for the 5 mm zone is 1.0 and for the 7 mm zone 0.8. In an evaluation of 100 patients post surgically, it has been found that weighting values for the 3 mm, 5 mm and 7 mm zones are equal, namely 1.0, 1.0, and 1.0 respectively. Subjective evaluation by the surgeon of each individual patient can influence him or her to assign weighting values between these two ranges. Hereafter we will proceed with illustration using the theoretical weighting coefficients 1.2, 1.0, and 0.8 for the 3 mm, 5 mm and 7 mm zones respectively.

The two semi-meridian values calculated using weighting coefficients for the 3 mm, 5 mm and 7 mm zones from topography allow for a more representative determinant of the corneal astigmatism. This provides parameters for the purpose of vector planning treatment and the reliable determination of corneal topographic astigmatism as well as a standard for corneal irregularity. These values can also be used pre and post operatively to gauge the success of astigmatic outcomes in patients undergoing refractive surgery.

In accordance with the invention, there is provided a method for determining parameter of magnitude and axis representing corneal astigmatism for use in vector analysis for diagnostic and surgical treatment, comprising producing a keratometric map of topographic measurements of each of two semi-meridians of the cornea of an eye, assigning weighting values to the topographic measurements in each of a plurality of zones in each semi-meridian, and vectorially combining the weighted values of the topographic measurements to obtain a vector parameter in each semi-meridian representing magnitude and axis of topographic irregularity which is adapted for use in diagnostic and surgical treatment.

In further accordance with the invention, the technique of vector planning combines corneal (topography) and refractive (wavefront) parameters to both reduce and regularize astigmatism in a single treatment step. The treatment is determined by first employing ocular residual astigmatism (ORA) to optimally reduce the astigmatic magnitude, followed by the regularization of the now reduced corneal astigmatism using a common refractive target for the two separate semi-meridians.

The calculated treatments are presented as a single asymmetric treatment application. In this way any astigmatism that cannot be eliminated from the optical system of the eye due to the prevailing ORA is both minimized and regularized.

The advanced vector planning technique of the invention can be used to treat naturally occurring irregular astigmatism by applying the treatment independently to each semi-meridian of the cornea. As a result the remaining astigmatism is optimally minimized and regularized leading to a reduction in ocular aberrations and subsequent potential for improvement in the best corrected visual activity.

Thus, in further accordance with the invention, there is provided a method for reducing and regularizing measured values of astigmatism in an eye of a patient to obtain target values for diagnosis and treatment of the patient, said method comprising the steps of: considering the cornea of an eye of a patient to be divided into superior and inferior semi-meridians; measuring corneal and refractive astigmatism values in each of the semi-meridians; determining topographic treatment parameters in each semi-meridian to maximally reduce the topographic astigmatism values in each of the semi-meridians based on minimizing ocular residual astigmatism in each semi-meridian and regularizing the thus reduced topographic treatment parameters using a common refractive parameter for the two separate semi-meridians to obtain in one step from said determining step to said regularizing step, final treatment target values for the two semi-meridians.

In still further accordance with the invention, there is provided apparatus for carrying out the method of the invention for obtaining surgical parameters comprising: means for obtaining target parameters representing topography of an eye in superior and inferior semi-meridians, means for obtaining a target parameter representing a refractive parameter for each semi-meridian, and a computer means for carrying out the steps of: determining target induced astigmatism vector parameters (TIA) for treating each semi-meridian by vectorially combining the topographic target parameters with the refractive parameter to obtain treatment vectors TIA in the two meridians which are equal and regularized.

BRIEF DESCRIPTION OF THE DRAWING

FIG. 1 is a topographic illustration of a cornea showing the flat and steep keratometry parameters in the 3 mm, 5 mm and 7 mm zones of the semi-meridians on Humphrey ATLAS topographer.

FIG. 2a is a Polar diagram showing the superior and inferior semi-meridian astigmatism values (unadjusted) for the 3 mm zone. (Scale ×2).

FIG. 2b is a double angle vector diagram in which astigmatism meridia is doubled for the 3 mm zone while magnitude remains the same and vectorial difference represents topographic disparity (TD) magnitude. (Scale ×2)

FIG. 4a is a Polar diagram showing weighted and unadjusted astigmatism values for each of the 3 mm, 5 mm and 7 mm semi-meridian in the corresponding inferior half of the cornea.

FIG. 4b is a double angle vector diagram showing a head to tail summation of the 3 mm, 5 mm and 7 mm weighted astigmatism parameters which are now doubled in angle to calculate the average inferior astigmatism parameter.

FIG. 6a is a double angle vector diagram showing the vector summation of the superior and inferior average weighted astigmatism values representing CorT (DAVD).

FIG. 6b is a Polar diagram showing the superior and inferior average weighted astigmatism values together with the CorT.

FIG. 6c is a tabular illustration showing the comparative effect of weighted and unadjusted astigmatisms for each zone of the superior and inferior semi-meridians.

FIG. 6d is a tabular illustration showing comparison between CorT and Sim K parameters.

FIG. 13a is a double angle vector diagram showing summation of optimal treatment vectors after regularization.

FIG. 13b is a double angle vector diagram showing applying the average treatment $TIA_{NET\ BC\times1}$ to each of the refractive targets (Target $R_B$) to achieve Target $R_C$, in which $TIA_{BC\times1}$=ORA at completion of stage 2 (B to C).

DETAILED DESCRIPTION OF THE INVENTION

Advances in computer assisted videokeratography (CAVK) have assisted the surgeon by providing detailed information regarding corneal shape. The keratometric view provided by topographers (FIG. 1) displays the corneal power and radius of curvature for different concentric zones of the cornea and provides more information than currently necessary for lasers that provide symmetric refractive corneal treatments. The keratometric view also customarily provides a Simulated Keratometry (Sim K) value that is a quantitative descriptor of corneal astigmatism at the 3 mm zone as an attempt to gain equivalence of corneal keratometry at the time of the introduction of the CAVK technology in the 1980's.

One commonly encountered difficulty with the Sim K value is that the algorithm that selects the meridian can on occasions be erratic where the bow tie demonstrates non-orthogonal characteristics. The topography device may be inconsistent in its choice of meridian ranging from either of the bow tie meridian or somewhere in between. The technique herein provides relevance and consistency in the corneal topography astigmatism value (CorT) by obtaining a vector summated mean magnitude and meridian from the keratometric view at three (inner, middle and peripheral) zones.

Currently no consistent values are offered by topographers that usefully represent the two semi-meridians of the cornea. Nor is there one astigmatism value that represents the whole cornea other than just the paracentral 3 mm region utilized by the Sim K magnitude and meridian value. These two vector semi-meridian values are necessary and useful parameters to derive this single value quantifying the astigmatism of the whole cornea. They are also essential for the vector planning of the asymmetric treatment process, to gauge irregularity and quantify the success of astigmatic outcomes by corneal parameters. The invention seeks to derive these values from the data currently available from corneal topographer maps as seen in FIG. 1.

Using the keratometric parameters from the 3 mm, 5 mm and 7 mm zones circumscribed from the central axis of the cornea (i.e., the area from 0-3 mm, from 3-5 mm and from 5-7 mm respectively), the semi-meridian values can be refined to more reliably identify the meridian and magnitude of the corneal topographical astigmatism by the process of vector summation.

Figure 2C:
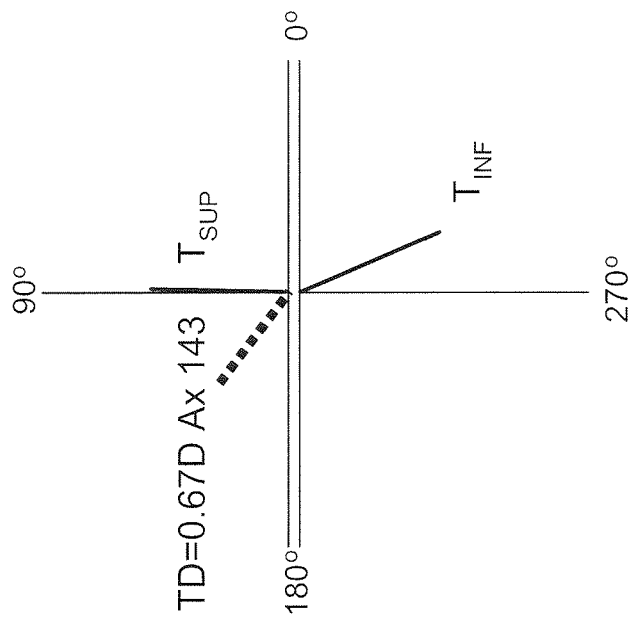
FIG. 2c is a Polar diagram in which the TD axis for the 3 mm zone is divided in half to display the direction as it would appear on the eye. (Scale ×2)

The topographic map in FIG. 1 displays two flat and two steep keratometric magnitudes together with their respective meridians for each of the three zones. The most applicable topographic reading for planning treatment and assessing potential astigmatic outcome is that of the 3 mm zone, as this is what predominantly coincides with the pupil and visual axis. Pairing up the most appropriate keratometric parameters for the 3 mm zone is determined by establishing the minimum magnitude of corneal irregularity or TD of the two pairs. That is, using one combination of flat/steep to determine the TD and comparing this in magnitude to the other combination of flat/steep to find the minimum of the two choices (FIGS. 2a, b and c).

Once the appropriate pairing is established for the 3 mm zone, the corresponding steep meridian in the 5 mm zone is determined by calculating the smallest angular difference between each of the steep meridians in the 5 mm zone relative to the 3 mm steep meridian determined from step 1 above. This is then repeated for the 7 mm zone, comparing the angular difference to the parameters of the 5 mm zone. The same process is then applied for the flat meridian. The magnitude of astigmatism for each zone is determined by the arithmetic difference between the flat and steep parameters for that zone, and its orientation is that of the steepest meridian.

Figures 3A, 3B:
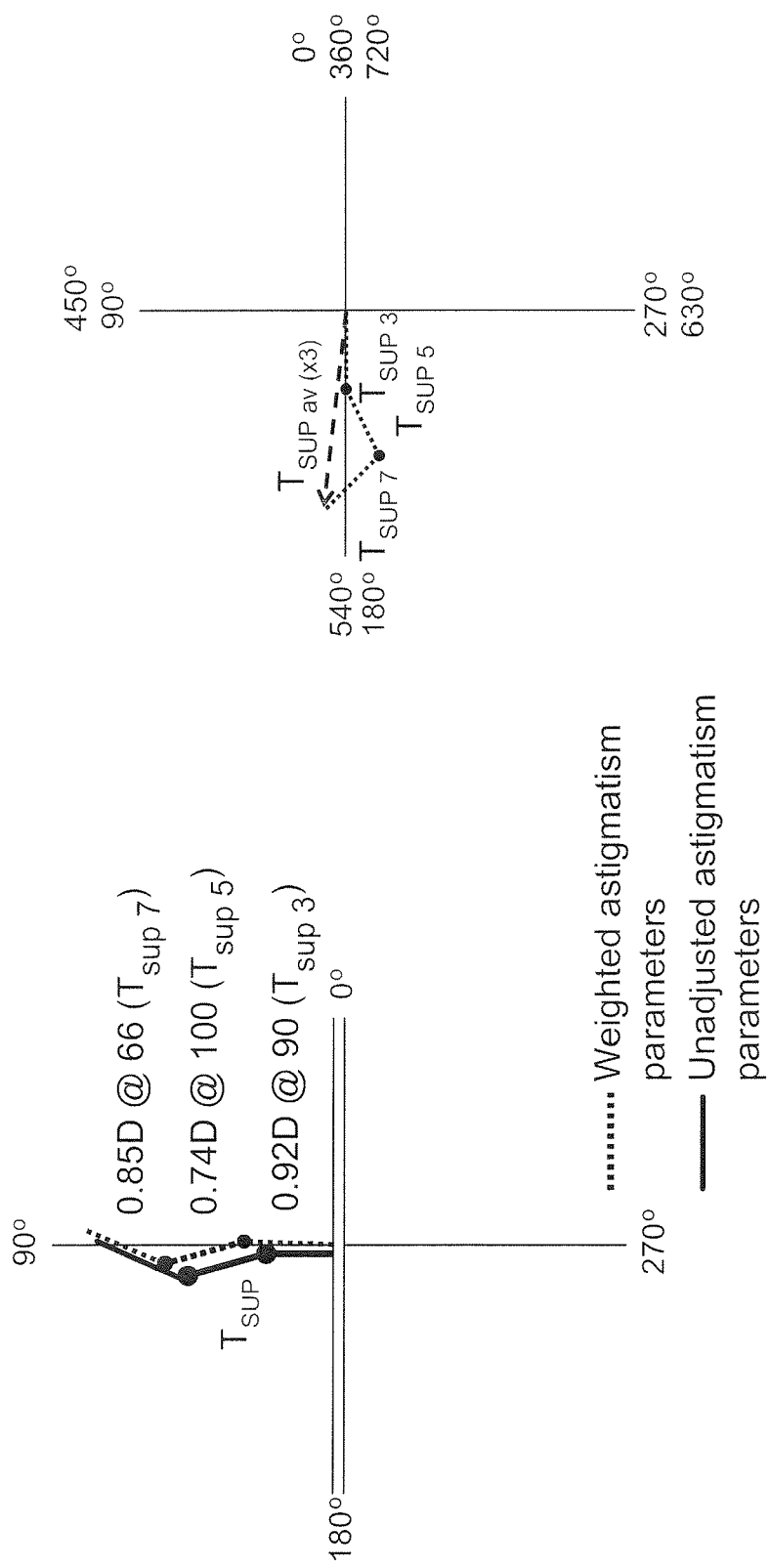
FIG. 3a is a Polar diagram showing weighted and unadjusted astigmatism parameters for each of the 3 mm, 5 mm and 7 mm semi-meridians in the corresponding superior half of the cornea.
FIG. 3b is a double angle vector diagram showing head to tail summation of the 3 mm, 5 mm and 7 mm weighted astigmatism parameters which are now doubled in angle to calculate the average superior astigmatism parameter.

The result is three astigmatism values for the superior semi-meridian of the cornea (3, 5 and 7 mm zones) and three for the inferior semi-meridian of the cornea (3, 5 and 7 mm zones). Based on the significance of the 3 mm, 5 mm and 7 mm zones in any surgical treatment paradigm, a weighting can be given to each zone, suitably increased for the inner and reduced for the outer with the middle unchanged: ×1.2 for the 3 mm (most applicable), ×1.0 for the 5 mm and ×0.8 for the 7 mm zone (least applicable) (FIGS. 3a and 4a).

Figure 5B:
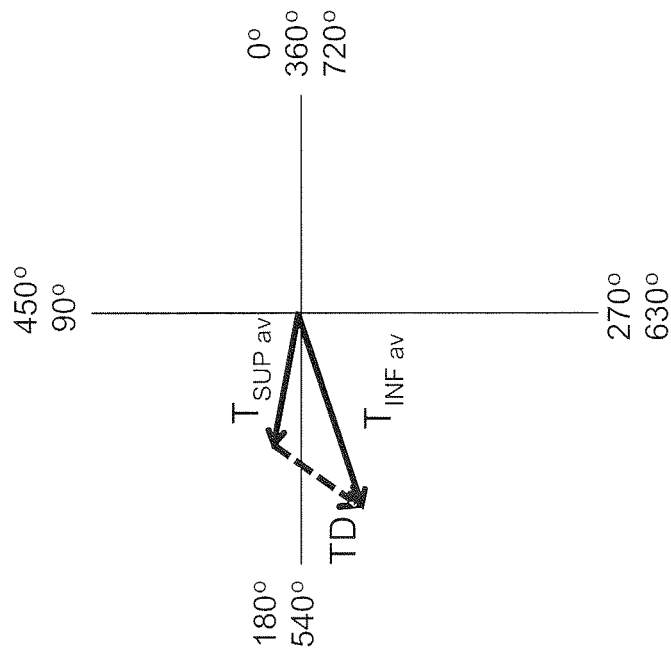
FIG. 5b is a double angle vector diagram showing the vectorial difference between superior and inferior average weighted astigmatisms which in calculated to be the TD (DAVD). (Scale ×2).
Figure 5A:
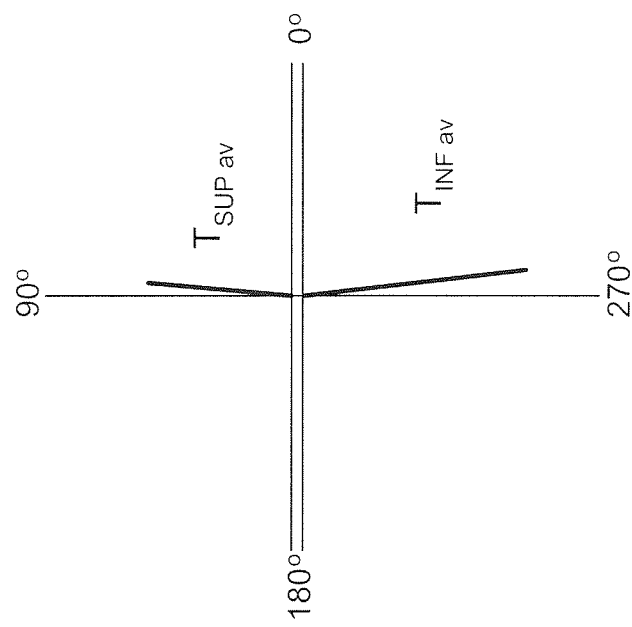
FIG. 5a is a Polar diagram showing the average superior and inferior weighted semi-meridian astigmatism values. (Scale ×2)

The polar diagram in FIG. 5a displays the two summated vector means as they would appear on an eye-one astigmatism in the superior semi-meridian and another in the inferior semi-meridian. These topographic astigmatism values will be used in vector planning as will be described later.

Figure 5C:
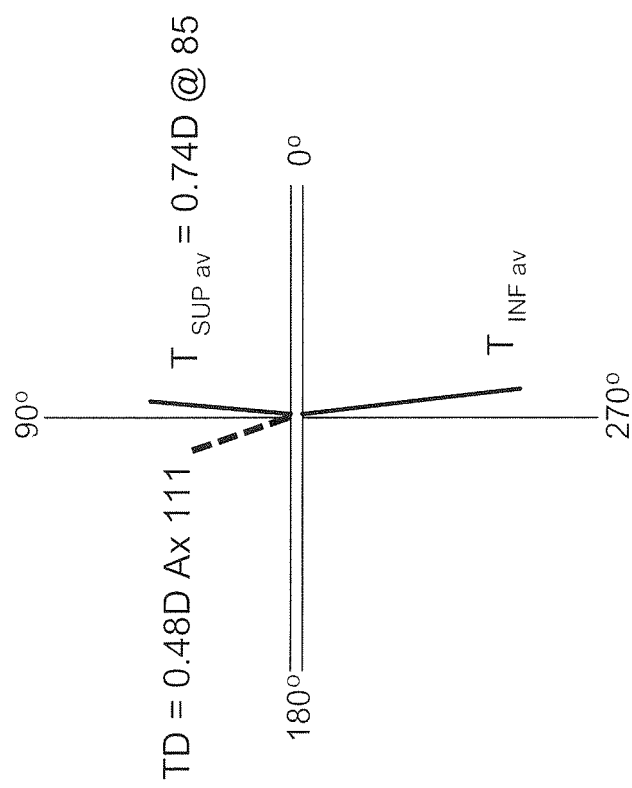
FIG. 5c is a Polar diagram showing the superior and inferior average astigmatisms from weighted parameters in corresponding corneal semi-meridians (Scale ×2). The TD is also displayed.

To determine the irregularity of the whole cornea, factoring in the weightings for the 3, 5 and 7 mm zones discussed above, the vectorial difference between these two astigmatisms is calculated by again doubling the axis on to a DAVD (FIG. 5b). The final meridian of the TD is determined by joining the resultant vector originating from the superior average astigmatism and terminating at the inferior average astigmatism on the DAVD and then being returned to the origin and halved to determine its actual direction. The corneal irregularity quantified in this way is termed Topographic Disparity (TD) and is expressed in diopters and degrees. This provides the value as it would appear on an eye (FIG. 5c).

To determine the total corneal topography astigmatism (CorT) as a representation of the whole cornea, a vector summated mean is calculated using the $T_{SUP}$ and $T_{INF}$ weighted values (FIGS. 6a and 6b). This describes the whole cornea as quantified by corneal topography with appropriate weightings to the 3, 5 and 7 mm zones such as presented in the example. This is preferential to the simulated keratometry value (Sim K) which is derived entirely from the 3 mm zone with variability and inconsistent bias sometimes demonstrated in the meridian selected.

The concentric corneal zones provided by the topography map (i.e. at 3 mm, 5 mm and 7 mm) are used to achieve two semi-meridian values, each representing one half of the cornea, and to weight the relevance of each zone and then determine corneal irregularity. This technique assesses the topographic disparity (TD)—a vectorial measure of irregular astigmatism, calculated as the dioptric distance between the displays of superior and inferior values on a 720 degree double-angle vector diagram (DAVD). A direct proportional relationship between increasing TD and ocular residual astigmatism (ORA) has been observed.

The ORA which quantifies the internal aberrations of the eye is calculated as the vectorial difference between corneal and refractive astigmatism parameters, and has a magnitude expressed in diopters and an orientation in degrees.

The relationship between TD and ORA has been shown to be significant in a group of 100 healthy astigmatic corneas prior to surgery. ORA and TD magnitudes of 0.75 D or less are considered to be normal with no impediment to achieving good astigmatic outcomes. Whereas magnitudes above 1.00 D might display a significant concern for the excess degree of internal aberrations or corneal irregularity with potential adverse outcomes, so that refractive laser or incisional surgery to correct astigmatism may be limited in the outcome achievable in correcting astigmatism. For this reason the surgeon may decide not to treat or to use vector planning as a treatment paradigm to optimize and reduce the resultant amount of corneal astigmatism remaining in such cases.

FIG. 6c displays the importance of the weighted summated vector means ($T_{SUP\ av}$ and $T_{INF\ av}$). The 7 mm zone unadjusted astigmatism magnitude is comparatively large at 1.74 D for the inferior semi-meridian, relative to the corresponding 1.06 D for the superior semi-meridian. In both the superior and inferior semi-meridian the 7 mm astigmatism values are larger than the 3 mm and 5 mm ones for the unadjusted parameters. The importance of a summated average vector is highlighted by the 'dampening' down of 0.06 D for the inferior semi-meridian, but only 0.01 D for the superior semi-meridian.

The summated vector mean of the two weighted semi-meridian values $T_{SUP\ av}$ and $T_{INF\ av}$ can be determined (FIG. 6d) to calculate an effective total corneal topography astigmatism described here_as the CorT value (0.91 D@91). Examining the relationship of the Sim K (0.88 D@102) to the Cor T value reveals similar magnitudes (both less than the arithmetic mean) this is likely a similar effect estimating the corneal topography astigmatism as a result of the steep meridian of the three zones not being inline. The meridian of the CorT value however aligns closer to the T sup (85 degrees) and $T_{INF}$ (275 degrees) in a clockwise direction and as a result is likely more representative of the total corneal astigmatism meridian by factoring in the influence of the 7 mm zone orientation. This difference of almost 10 degrees (CorT meridian of 91 degrees compared to Sim K meridian of 102 degrees) would be a significant amount to factor in during surgical incision or laser planning.

It is important to note that the greater the lack of linearity of each of the individual components in the three zones, the less the effective regular astigmatism represented by Sim K or CorT. The values of 20% increase and decrease from unity for the inner and outer zones respectively is an example which is empirically estimated at this stage and could be modified in the future according to experience and population studies. The sum of the three weighted zone values of 3.0 D is equal to the sum of the three unadjusted unity values so that no net increase or decrease of astigmatism results from this adjustment process.

The closeness of the Sim K magnitude and weighted CorT magnitudes also demonstrates the parallel effect of this non linear phenomenon, and how effectively the CorT represents the whole cornea. Of particular benefit of CorT is accuracy and consistency in identifying the most relevant meridian by employing the vectorial sum and mean of the $T_{SUP}$ and $T_{INF}$ semi-meridian components.

The technique provides additional safety where corneal parameters are included in the refractive treatment plan using vector planning. Vector averaging of multiple values reduces the effect of any measurement artefact or actual outliers that may occur in an automated measurement process such as CAVK.

This method of calculating semi-meridian values to quantify corneal astigmatism incorporates the keratometric magnitudes and meridian of each of the 3 mm, 5 mm and 7 mm zones from both halves of the cornea. These two semi-meridian values can in turn undergo vector summation to provide a corneal topography astigmatism value—the CorT that quantifies the overall corneal astigmatism of the eye as determined by corneal topography. This value may have benefits over Sim K values currently employed. The semi-meridian values calculated can also provide a vectorial value for corneal irregularity—the topographic disparity. This together with the ORA value, can be used in the consulting suite as fundamental preoperative parameters to determine patient suitability and potential for good visual outcomes when planning refractive surgery to correct for astigmatism.

The technique described also allows for adjusted weighting to be given to values closer to or further from the visual axis, by providing a factor to apportion greater or lesser relevance to their magnitudes at the measured meridian. The derived semi-meridian values, each representing one half of the cornea, can be incorporated as treatment parameters to accurately quantify the corneal astigmatism required to resolve with refractive parameters in the vector planning treatment process. Combining corneal and refractive parameters in the vector planning process for the concurrent treatment of idiopathic irregular astigmatism using these semi-meridian values, can potentially lead to greater consistency in corneal astigmatism outcomes, providing the opportunity for further refinement of overall visual outcome quality in the routine laser vision correction process.

Using the parameters in FIG. 1:

Step 1. Determine the appropriate pairing of flat and steep meridian.

To determine the appropriate pairing of flat and steep parameters calculate the minimum TD magnitude from the values in the 3 mm zone.

First pairing (FIGS. 2a, 2b and 2c)—
40.46/41.23@90 (0.77 D@90) superior semi-meridian
40.68/41.54@294 (0.86 D@294) inferior semi-meridian
TD=0.67 D Alternative pairing—
40.68/41.23@90 (0.55 D@90) superior semi-meridian
40.46/41.54@294 (1.08 D@294) inferior semi-meridian
TD=0.82 D The first pairing has the lower irregularity value so is selected to provide adjusted astigmatism values for zones.

Step 2. Apply the appropriate weightings to the flat/steep parameters selected from (i). (FIGS. 3a and 4a)

3 mm zone:
0.77 D@90 (superior semi-meridian)×1.2 (weighting for 3 mm zone) =0.92 D@90
0.86 D@294 (inferior semi-meridian)×1.2 (weighting for 3 mm zone)=1.03 D@294

Step 3. Match up the corresponding steep and flat keratometry readings in the 5 mm zone by selecting the ones closest by angular separation to that in the 3 mm zone.

5 mm zone:
41.13/41.87@100 (0.74 D@100) superior semi-meridian
0.74 D@100×1.0 (weighting for 5 mm zone)=0.74 D@100
41.17/42.45@276 (1.28 D@276) inferior semi-meridian
1.28 D@276×1.0 (weighting for 5 mm zone)=1.28 D@276

Step 4. Again match up the corresponding steep and flat keratometry readings for the 7 mm zone by selecting the ones closest by angular separation to that in the 5 mm zone.

7 mm zone:
42.18/43.24@66 (1.06 D@66) superior semi-meridian
1.06 D@66×0.80 (weighting for 7 mm zone)=0.85 D@66
42.30/44.04@260 (1.74@260) inferior semi-meridian
1.74 D@260×0.80 (weighting for 7 mm zone)=1.39 D@260

Step 5. Head-to-tail summation is used to calculate the resultant superior and inferior semi-meridian average astigmatism (FIGS. 3b and 4b).

Summated vector mean superior astigmatism=0.74 D@85
$T_{SUP\ av}$
Summated vector mean inferior astigmatism=1.10 D@275
$T_{INF\ av}$
(FIG. 5a).

Step 6. Vectorial difference $T_{SUP}$ and $T_{INF}$.

Doubling the meridian of the average superior and inferior vector mean astigmatism ($T_{SUP\ av}$ and $T_{INF\ av}$ and determining the vectorial difference on a DAVD provide the corneal irregularity or TD in diopters and degrees.

TD=0.48D Ax 111 (FIGS. 5b and 5c).

Step 7. Vectorial addition $T_{SUP}$ and $T_{INF}$ for CorT value.

Head to tail summation of superior and inferior astigmatism values to derive a corneal topography astigmatism value (CorT) which is represented on both semi meridian with equal magnitudes and 180 apart.

0.91 D@91
0.91 D@271

Significant ocular aberrations can reduce the quality and quantity of vision resulting in symptoms of glare, haloes, star bursting of light at night and an overall reduction in best corrected visual acuity. These commonly occur in cases of irregular astigmatism and can be measured in quantified by aberrometry. An accurate gauge of aberrations can also be calculated by vectorial differences in corneal and refractive astigmatic values to quantify the internal (non-corneal) aberrations.

The technique of vector planning is a systematic paradigm that enables the combination of corneal parameters with refractive parameters for the optimized treatment of astigmatism.

Advanced vector planning allows for treatment of naturally occurring irregular astigmatism using LASIK or PARK for each semi-meridian of the cornea. The process provides potential for improvement in visual outcomes over the exclusive use of either topographic or wavefront refractive values.

There is commonly a difference between corneal and refractive astigmatism magnitudes and/or axes. In such cases this is quantified by the ocular residual astigmatism (ORA). The ORA is a calculated vectorial value that quantifies intraocular aberrations due to differences between topographical and second order aberrometry astigmatism. Higher amounts of ORA are directly proportional to larger amounts of topographic disparity (TD) as previously shown as a calculated vectorial value to quantify corneal irregularity. Reducing ocular aberrations by minimizing the resultant ORA using vector planning can improve the visual performance of an eye.

The technique of applying vector planning independently to each semi-meridian of the cornea is described hereafter.

To further improve current astigmatic and visual outcomes in excimer laser surgery two treatment principles are paramount. Firstly, the total sum astigmatism as examined both topographically and refractively is maximally reduced (which will be a minimum value quantified by the ORA). Secondly, the minimum astigmatism remaining on the cornea is preferentially left in a regular state. These two principles have heretofore been separately detailed for naturally occurring regular and irregular astigmatism.

Vector planning enables maximum reduction of astigmatism in such a way that the sum of the resultant topographic and refractive astigmatic targets (i.e. the ORA) is at a minimum for that individual eye's unique parameters. This remaining astigmatism is best apportioned between the topographic and refractive modalities in an optimized manner. The net effect is to leave less astigmatism remaining on the cornea and potentially achieve a better visual outcome with reduced lower and higher order optical aberrations.

Naturally occurring irregular astigmatism is widely prevalent in the population presenting for laser surgery and can be quantified using the TD evaluation. This vectorial value has a magnitude and axis, and is expressed in diopters as previously explained with 43% of eyes in a previous study having a value of greater than 1.00 D. It is calculated as the separation between the two opposite semi-meridian astigmatic values representing each half of the topography map on a 720 degree double angle vector diagram (DAVD) (FIGS. 1a, b and c). Note the relevant direct relationship observed that the higher the irregularity (TD) of a cornea the greater is the ORA.

To maximally reduce the astigmatism, one common value for refractive astigmatism (manifest or wavefront) can be resolved separately with two differing topographic astigmatism values; one for each semi-meridian of the cornea as shown, for example, in FIGS. 6a to d. FIG. 6d shows CorT as an arithmetic average of $T_{SUP\_A}$ and $T_{SUP\_A}$ which best represents the corneal astigmatism using the weighted 3 mm, 5 mm and 7 mm values. Current modes of practice using wavefront or manifest refraction only ascertain a single refractive cylinder value for the entire eye including the cornea. The additional step of regularization of the resultant reduced but still irregular corneal astigmatism is beneficial to achieve an orthogonal and symmetrical cornea and hence achieve the best visual potential for an eye.

The treatment process, according to the invention, sequentially combines the two fundamental treatment steps into one. Firstly, maximally and optimally reducing the astigmatism (step from A to B) employing both topographic and wavefront parameters in an optimized manner, followed secondly by the regularization of the remaining corneal astigmatism (step from B to C); these two separate steps can be merged into a single step treatment process, calculated at the final orthogonal symmetrical targets C from the preoperative astigmatism state of A.

Treatment Paradigm for Naturally Occurring Irregular Astigmatism

1. The optimal reduction of astigmatism (step A to B).

Figure 7B:
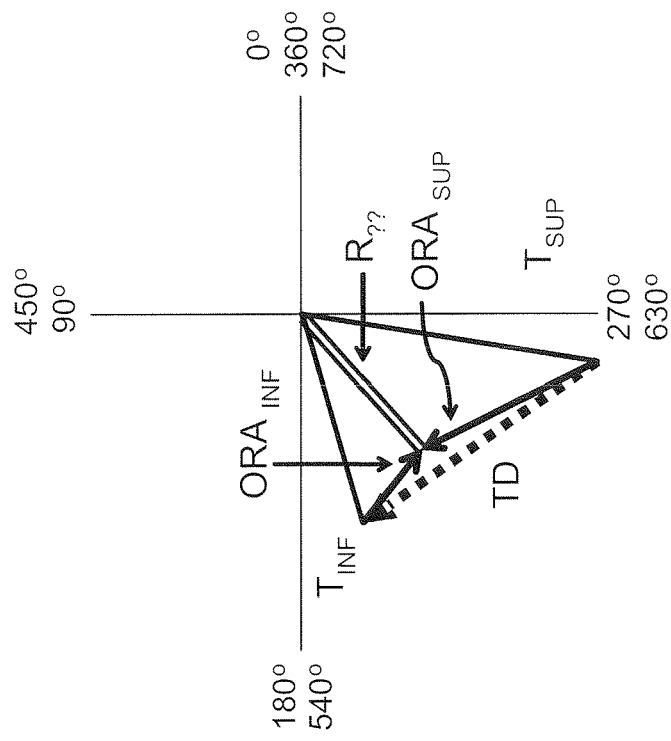
FIG. 7b is a double angle vector diagram showing the parameters of FIG. 7a as vectors displayed at 2× angle.
Figure 7A:
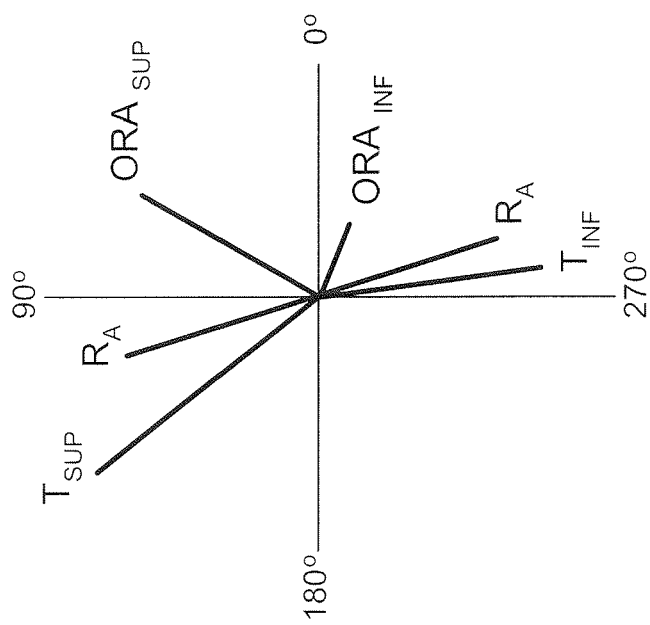
FIG. 7a is a polar diagram illustrating topographic disparity (TD) representing vectorial measure of irregularity as it would appear on the eye.
Figure 7C:
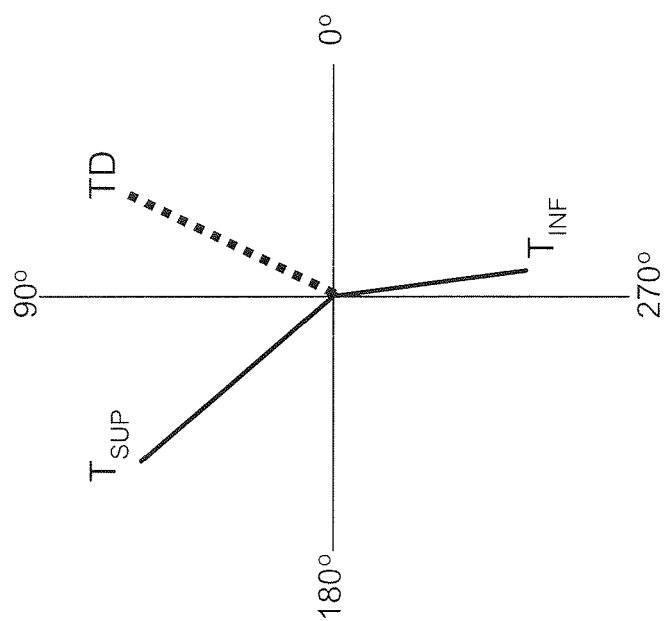
FIG. 7c is a polar diagram illustrating topographic disparity (TD) representing a vectonal measure of irregularity as it would appear on the eye.

FIG. 7a displays a 360 degree polar (not vector) diagram of astigmatism parameters as measured by topography and refraction, in which the two pre-operative measurements do not correspond with each other in magnitude or orientation. The corneal astigmatism is irregular as the superior topographic semi meridian value ($T_{SUP}$) differs from the inferior topographic semi meridian value ($T_{INF}$) both in magnitude and orientation as shown in FIG. 6, hence making it both asymmetrical and non-orthogonal. The refractive astigmatism (R), using wavefront (second order Zernike 3 and 5 cylindrical astigmatism) or manifest parameters, is displayed as a common symmetrical orthogonal value for the superior and inferior corneal semi-meridians.

Calculation of the ORA

The first parameter that requires calculation to maximally reduce the existing astigmatism is the ORA—this is the vectorial difference between the refractive and corneal astigmatism at the corneal plane.

The existing astigmatism can be quantified by the simple arithmetic sum of the refractive and topographic components. This quantifies the sum total astigmatism to be corrected, and what proportion is uncorrected as quantified by the ORA. In the presence of corneal irregularity, the ORA can be calculated separately for each of the two semi meridians as shown in FIG. 7a wherein the ORA is the vectorial difference between the topographic and refractive parameters for each semi-meridian. The neutralization of the ORA must occur either on the cornea or in the spectacles, or in this case where operative parameters are optimized, a combination of the two (FIG. 8 displays the corresponding treatment vectors). The emphasis chosen here for apportioning correction of the ORA is 40% topographic and 60% refractive—this has previously been calculated as an average and used in a vector planning study.

The apportioning of each can vary from case to case and is dependent on the proportional theoretical topographic and refractive targets the surgeon is aiming to achieve. Where possible these targets should aim at reducing the corneal astigmatism to 0.75 D and the spectacle refraction cylinder to 0.50 DC or less. In cases where this is not achievable because the ORA is greater than 1.25 D then another emphasis option as previously may be appropriate. Regardless of the emphasis placed on how to optimally deal with the ORA, the maximum amount of astigmatism is being treated in the optical system of any eye when the sum of the topography and refractive astigmatism targets equal the ORA. Calculating the ORA prior to surgery allows the maximum amount of astigmatism to be treated and the amount left on the cornea minimized to more acceptable levels.

Figure 9A:
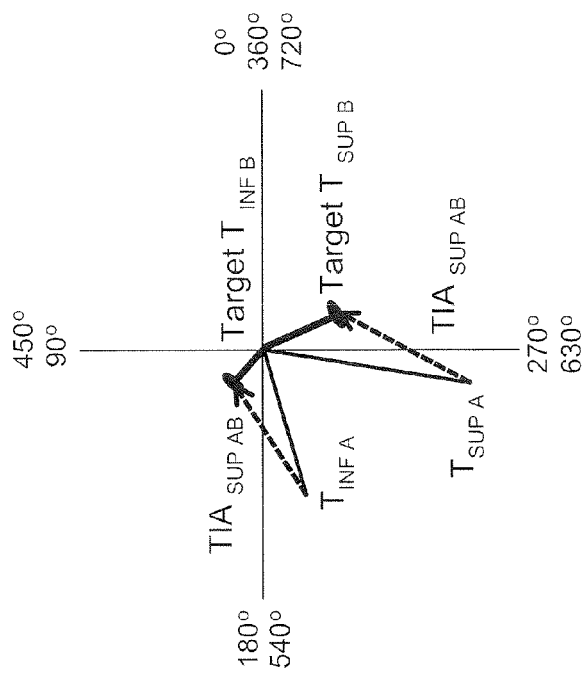
FIG. 9a is a double angle vector diagram showing the component in FIG. 8 with their magnitudes and axis.
Figure 9B:
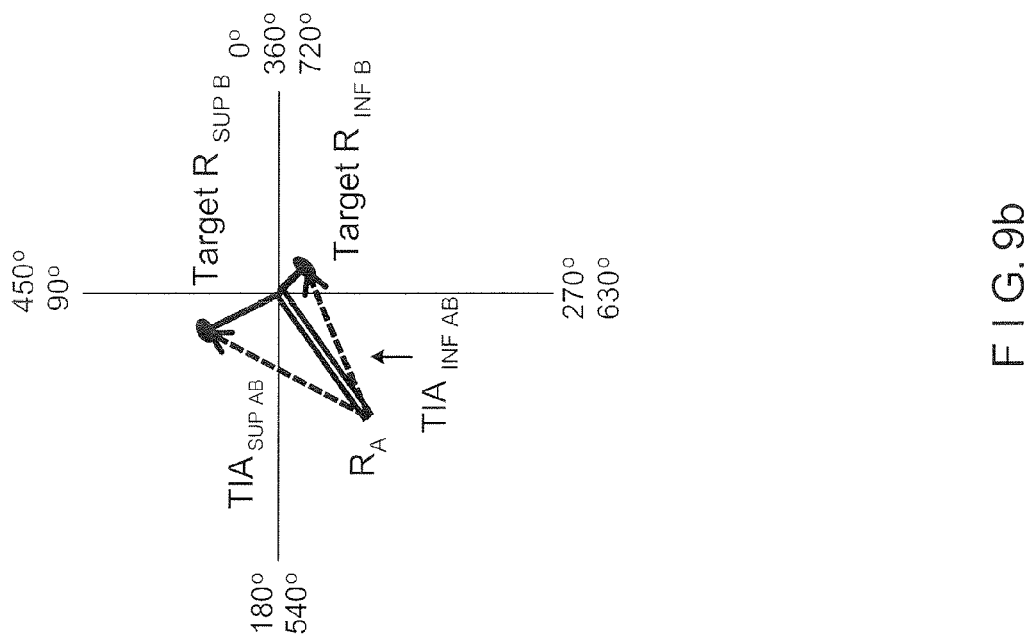
FIG. 9b is a double angle vector diagram after treatment of the components along with respective magnitudes and axes.

Calculation of Treatment (TIA) to Optimally Reduce Astigmatism with Minimum ORA Remaining The target induced astigmatism vector (TIA) for astigmatic treatment for each semi-meridian is a steepening effect and hence is aligned with the axis that is being maximally ablated. The TIA is the vectorial difference, or the treatment required between the preoperative astigmatism and the target which it identifies. This treatment vector can be applied separately, to each semi-meridian, $TIA_{SUP\ AB}$ and $TIA_{INF\ AB}$ differing both in magnitude and meridian due to the differing topographic values T representing each semi-meridian. This can be represented on a DAVD—that is, the TIA vectors are doubled in axes with no change in magnitude and then applied to their corresponding preoperative topography values (on the DAVD at two times their steep meridian). This results in topographic targets (Target $T_{SUP\ B}$ and $T_{INF\ B}$) of the astigmatic reduction from A to B which still remain asymmetrical and non-orthogonal (FIG. 9a). The same process can be applied to the common refractive astigmatism using the treatment vectors $TIA_{SUP\ AB}$ and $TIA_{INF\ AB}$ to achieve two refractive targets (FIG. 9b)—one for each semi-meridian—although in practice only one refractive target is utilized.

Figure 10:
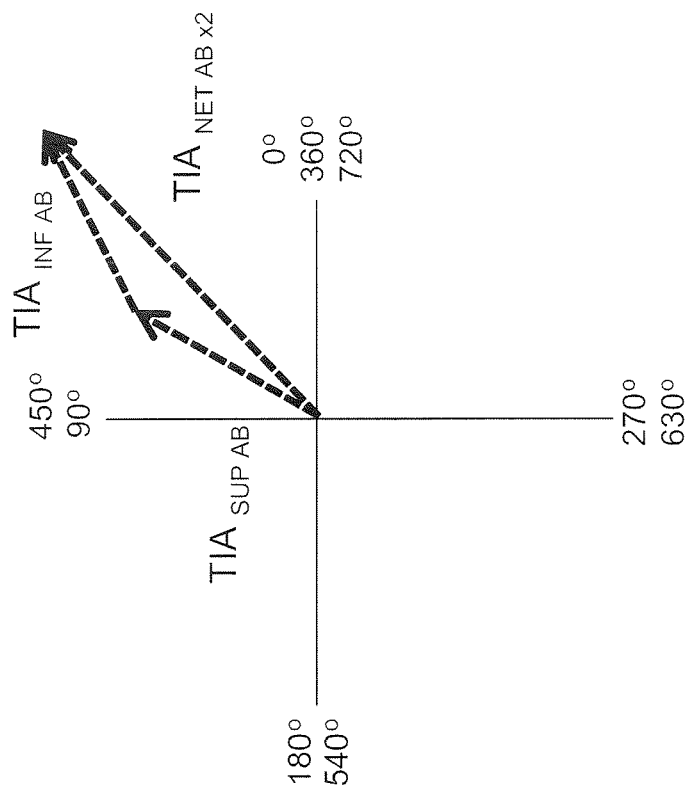
FIG. 10 is a double angle vector diagram showing treatment of the vectors together with magnitudes and axes thereof.
Figure 11A:
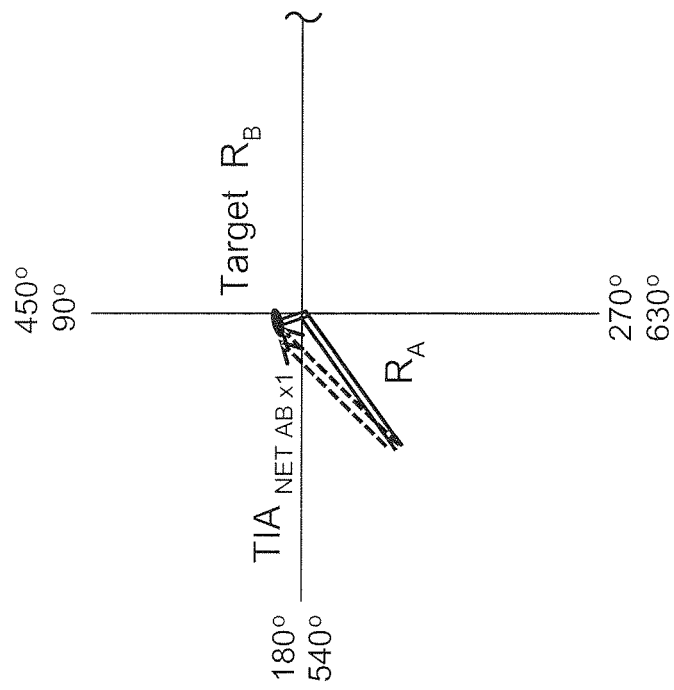
FIG. 11a is a vector diagram illustrating regularization of non-orthogonal astigmatism together with values of magnitude and axes.
Figure 11B:
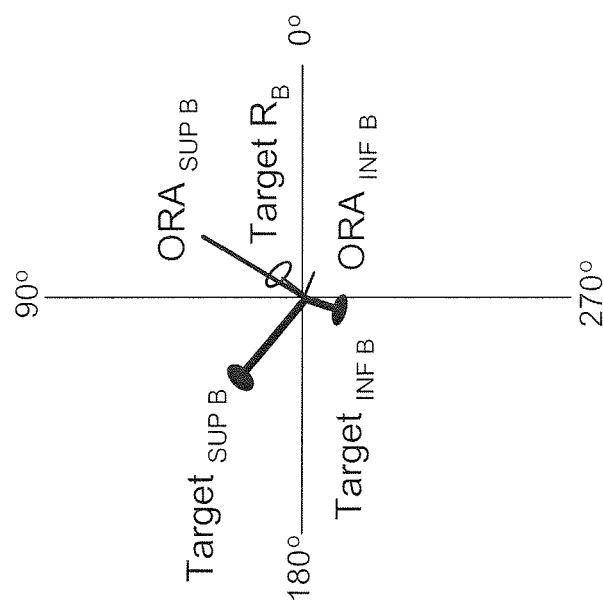
FIG. 11b is a polar diagram showing the refractive and topographic targets including the resultant ORA for each semi-meridian from step AB.

To determine the symmetric refractive cylinder target (Target $R_B$) the net overall treatment effect ($TIA_{NET\ AB\ \times 2}$) is calculated by summating the applied $TIA_{INF\ AB}$ and the $TIA_{SUP\ AB}$ in a head to tail manner on a DAVD (FIG. 10) FIG. 10 shows DAVD showing summation of optimal treatment vectors $TIA_{SUP\ AB}$ and $TIA_{INF\ AB}$) to calculate average applied treatment ($TIA_{NET\ AB\ \times 2}$) to refractive astimatism. The $TIA_{NET AB \times 2}$ magnitude is then divided by two due to the addition of the two vectors $TIA_{SUP\ AB}$ and $TIA_{INF\ AB}$. The $_{TIA\ NET AB \times 1}$ (halving the magnitude since two parameters are summated) is then applied to each of the semi meridional displays of the preoperative cylindrical refraction (FIG. 11a displays the orthogonal and symmetrical 'superior' and 'inferior' refractions as a pair—which overlie one another on a DAVD as they are 360° apart) resulting in the one common refractive target (Target $R_B$)' This together with the resultant refractive and topographic targets together with the superior and inferior ORA are displayed in FIG. 11b.

This optimized outcome is for the minimum amount of astigmatism to remain—this is equal to the ocular residual astigmatism (ORA) normally addressing the internal aberrations of the whole eye and in this case calculated separately for each semi-meridian.

Regularization Step (Step B to C) with Minimum Remaining ORA

Figure 12A:
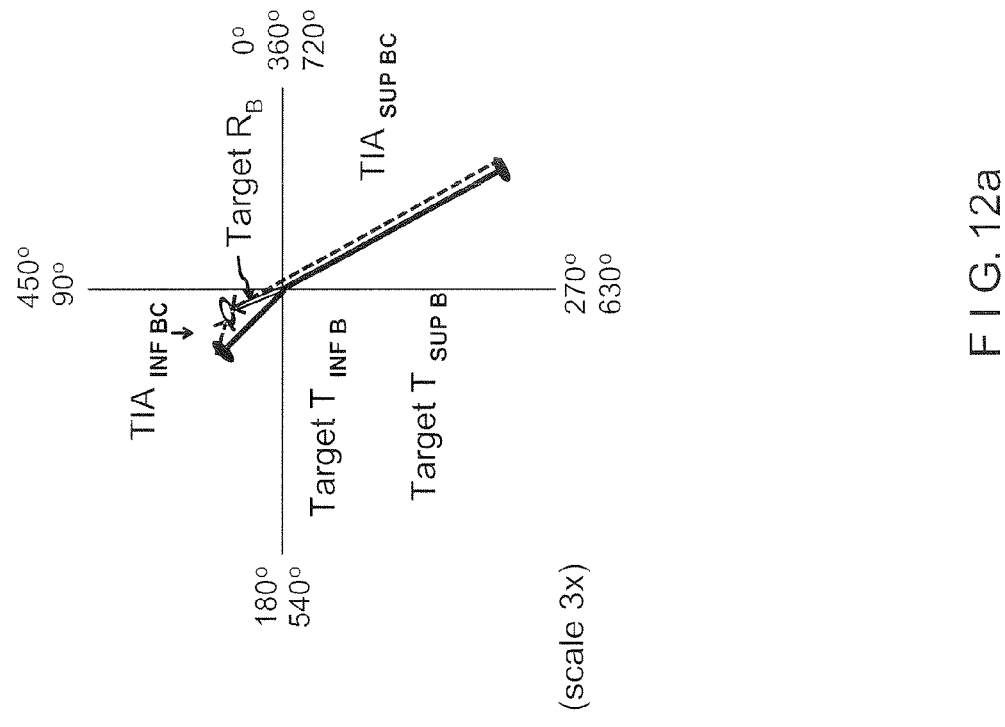
FIG. 12a is a double angle vector diagram showing regularization of non-orthogonal astigmatism after maximum treatment of astigmatism (step AB) by shifting the topography targets to the common refractive target (Target $R_B$) achieved in which this is step B to C (BC).
Figure 12B:
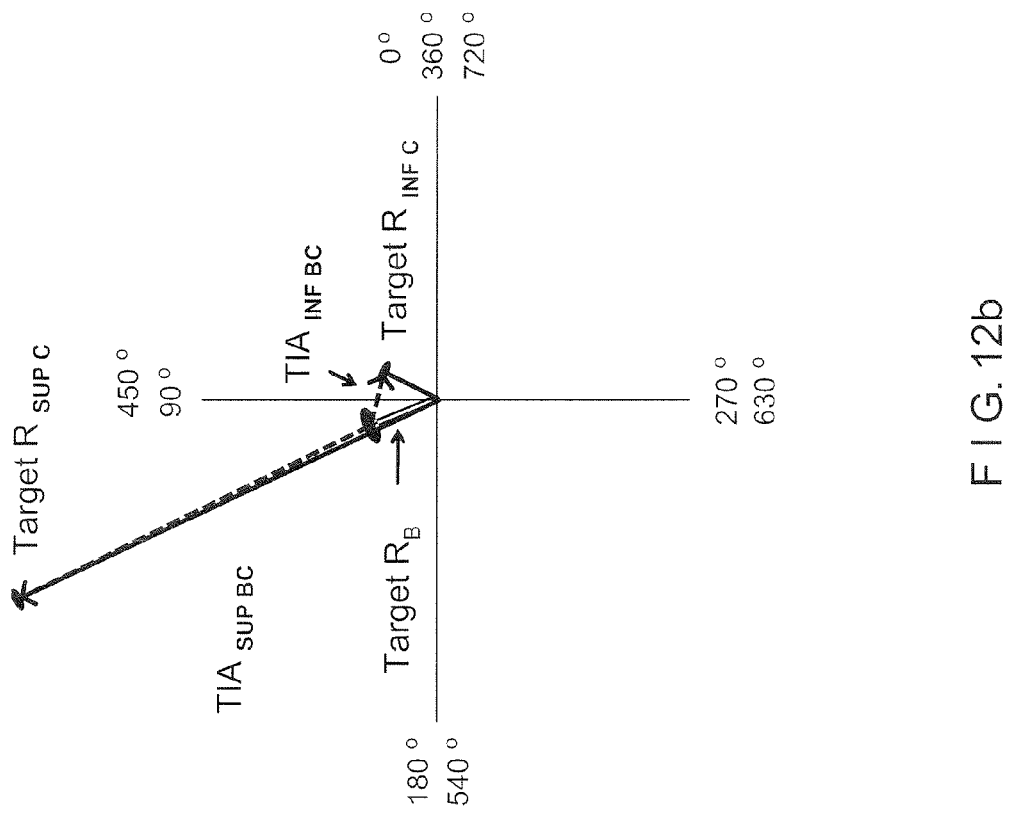
FIG. 12b is a double angle vector diagram showing the refractive targets achieved (Target R) after applying the treatment for the regularization of non-orthogonal astigmatism to the common refractive target (Target $R_B$) achieved from the maximum treatment of astigmatism (step AB).

A second treatment ($TIA_{SUP\ BC}$ and $TIA_{INF\ BC}$) can then be applied to each corresponding corneal target achieved from the optimal reduction of astigmatism above (Target $T_{SUP\ B}$ and Target $T_{INF\ B}$) to achieve a symmetrical and orthogonal corneal astigmatism outcome This is done by targeting the refractive cylinder target (Target $R_B$) achieved from the first step (step A to B) as shown in FIG. 12a. The resultant refractive targets for the superior and inferior semi meridians are displayed in FIG. 12b. The final symmetrical refractive cylinder target (Target $R_C$) from the second step (B to C) of regularization is calculated by again averaging the superior and inferior $TIA_{BC}$ in a head to tail manner and adding this value ($TIA_{NET BC\times 1}$) to Target $R_B$ (FIGS. 13a and 13b) resulting in the common refractive cylinder and the topography being aligned as displayed in FIG. 14.

Figure 14:
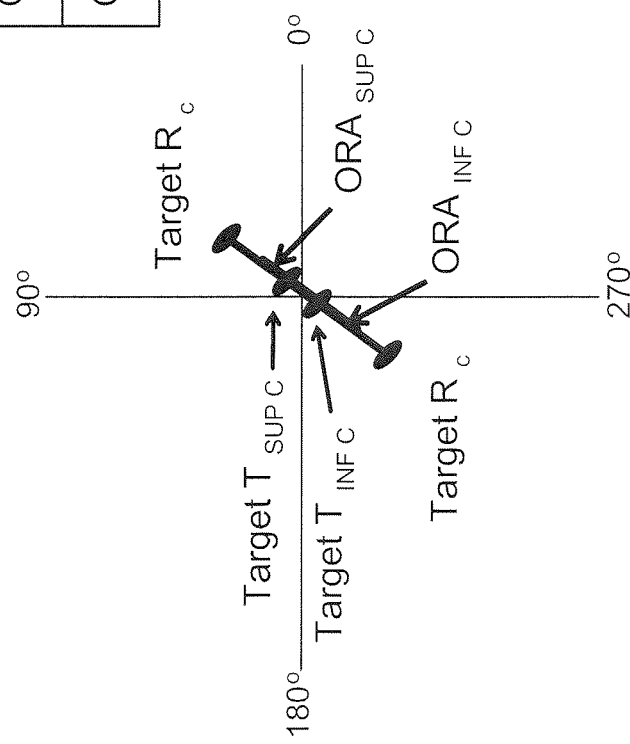
FIG. 14 is a polar diagram showing topography and refractive targets after maximum treatment of astigmatism (AB) and regularization (BC) by shifting the topography targets to the common refractive target (Target $R_C$), in which the ORA in this case is an arithmetic difference between the refractive and topographic targets due to zero difference in axes between the two.

This refractive change from B to C by the treatment $TIA_{NET BC\times 1}$ to each of the Target $R_{B's}$ effectively quantifies each of the separate ORAs ($ORA_C$) to be the minimum possible defined in the same step as regularizing the cornea (FIG. 14).

FIG. 10 shows DAVD showing summation of optimal treatment of the vector together with magnitudes and axes thereof.

Maximum Optimized Reduction and Regularization in One Step (A to C)

Figure 15:
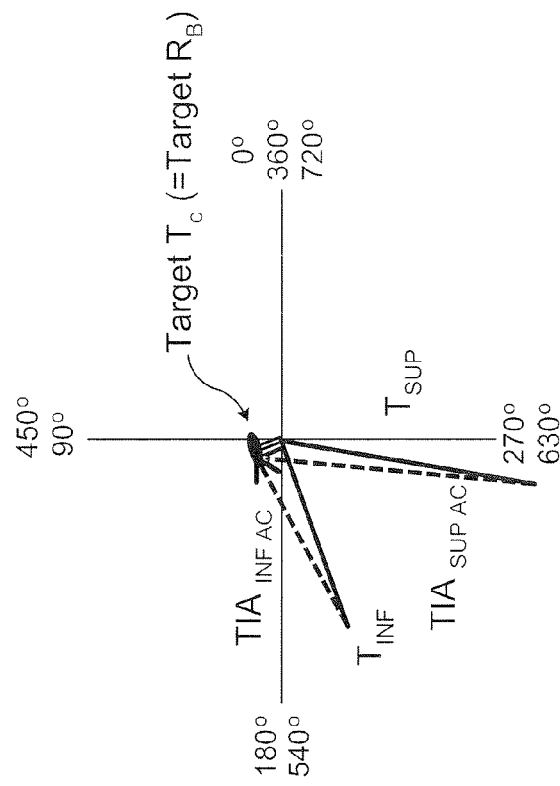
FIG. 15 is a double angle vector diagram showing the treatment applied ($TIA_{SUP\ AC}$ and $TIA_{INF\ AC}$) to the two preoperative corneal parameters ($T_{SUP\ A}$ and $T_{INF\ A}$) to achieve reduction and regularization of the cornea in one surgical step [step A to C (AC)] of the preoperative.
Figure 16:
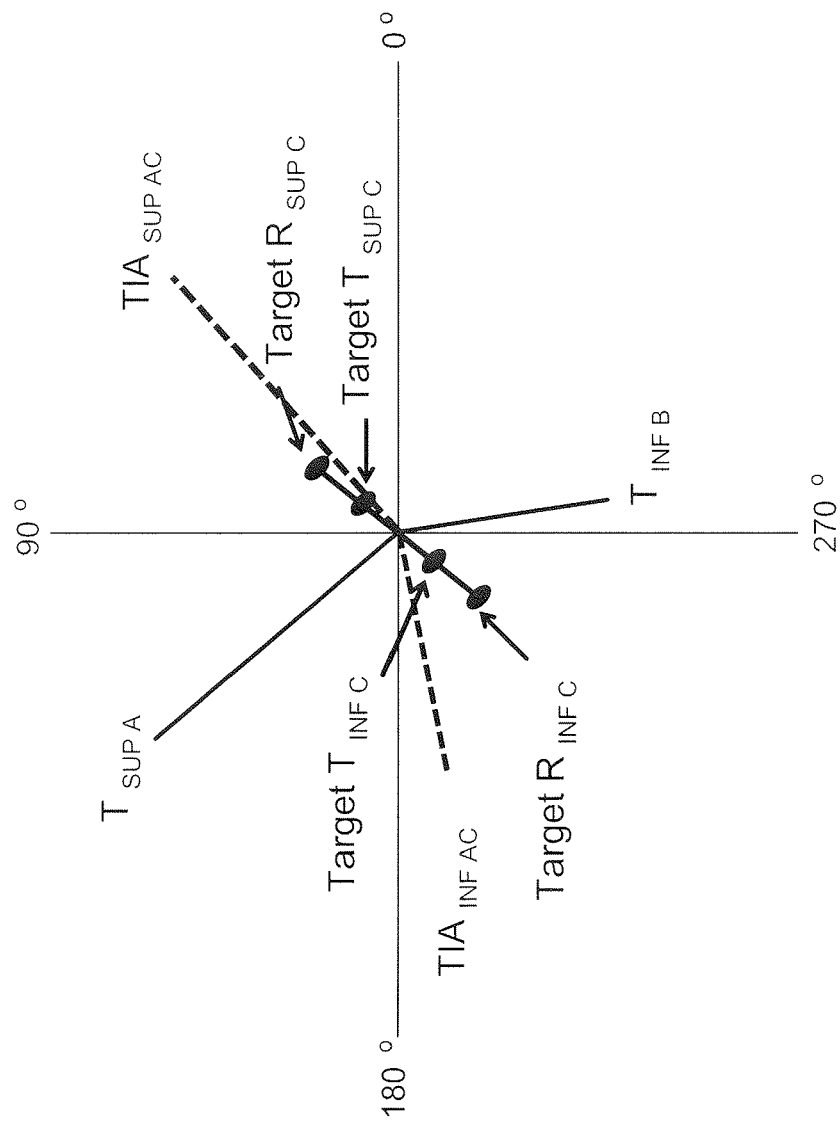
FIG. 16 is a polar diagram showing preoperative topography and with refractive and topographical targets after maximum treatment of astigmatism and regularization in a single surgical step.

The semi meridian treatments required to achieve in one step the maximum optimized reduction of astigmatism together with a symmetrical, orthogonal cornea ($TIA_{SUP\ AC}$ for superior semi meridian and $TIA_{INF\ AC}$ for inferior semi meridian) is calculated by targeting the target refraction from step A to B (Target $R_B$) achieved from the first process of maximally and optimally reducing the existing corneal irregular astigmatism. These treatments are then applied to both the preoperative corneal values ($T_{SUP\ A}$ and $T_{INF\ A}$) as displayed in FIG. 15 to achieve the goal in one surgical treatment step of reduction and regularization. FIG. 16 displays the superior and inferior treatments together with the refractive and topographic targets after maximum treatment of astigmatism and regularization in a single surgical step.

The function of a transparent cornea can be compared to the properties of a clear window pane. Just as warpage in a flat pane of glass causes distortion of transmitted contours for the observer when looking through it, so too does irregularity of the cornea reduce the equally spaced arrangement of parallel light rays that pass through it. The distortion experienced when looking through an irregular cornea can be displayed on an aberrometer using a point spread function of an image of light passing through the cornea with existing elevated high order astigmatisms (HOAs}.

In the commonly practised symmetrical treatment of corneal astigmatism, whether the astigmatism is regular or irregular, differences commonly exist between corneal and refractive astigmatism values. Conventional treatment by refractive values alone leaves all the non-corneal astigmatism (quantified by the ORA) remaining on the cornea to neutralize the internal aberrations of the eye. This can amount to more than one diopter in more than 30% of eyes treated by laser vision correction for myopia and astigmatism and more than the preoperative existing corneal astigmatism in 7% causing an overall increase in astigmatism as a result of the surgery.

Similarly the net effect of treatment by wavefront parameters alone is an excess of astigmatism left on the corneal surface than is otherwise necessary. A second undesirable effect of aberrometric treatment of HOAs is the necessity to create irregularities on the corneal surface to neutralize those that lie behind it on the light's optical pathway to the retina without specifically attempting to regularize the cornea.

There is no question that wavefront aberrometry is an important and useful diagnostic modality to create an aspheric cornea and improve the spherical visual outcome in patients with large pupils and significant HOAs. However, an inherent disadvantage of the technology is that the aberrations measured and permanently neutralized on the corneal surface may be lenticular or perceptive, and so create a permanent change based on variables that are not stable over time.

The significance of these higher level disorders may be visual cortex and/or occipital perceptions of astigmatism at the visual cortex that influence the manifest refraction is substantially unmeasured and excluded from treatment using aberrometry alone. These non optical astigmatic influences can have a significant effect on the treatment applied to the cornea and its resultant shape when the manifest refraction is the exclusive guiding paradigm. In conventional refractive treatments these are not moderated by any topographic input at all.

There are major theoretical and practical obstacles to the dependence upon wavefront values being used alone as a treatment modality which has also been recognized by other authors. The key benefit of vector planning in the treatment process is the ability to combine preoperative corneal astigmatism parameters with those for refractive wavefront astigmatism in a systematic manner. In this way, the cornea can be protected against astigmatism considered to be unfavorable (such as against-the-rule or oblique), and so avoid excess astigmatism remaining in such cases and its consequent higher order aberrations such as coma or trefoil. Using the technique described, any unavoidable ORA that does remain neutralized on the cornea can be left in an orthogonal symmetric (regular) state, resulting in reduced distortion of parallel light rays as they pass through the cornea. In this manner an optimal visual outcome is possible with both reduced and regularized corneal astigmatism and potentially reduced aberrations.

Figure 8:
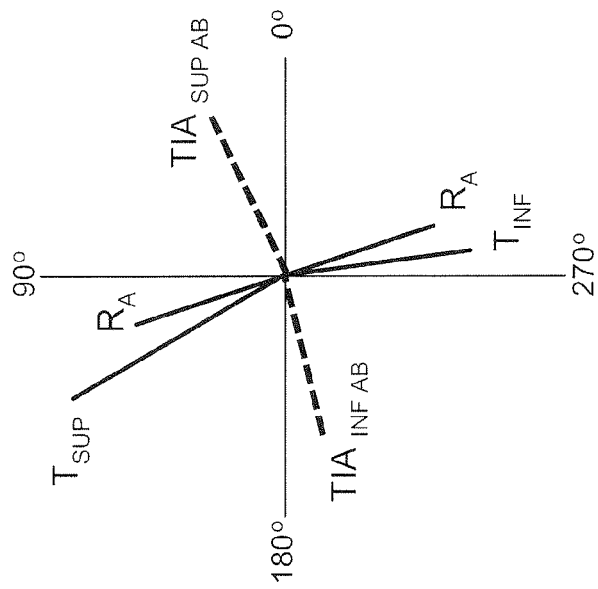
FIG. 8 is a polar diagram illustrating the treatment of astigmatism and the values of various components.

FIGS. 8 and 9 display the maximum reduction of astigmatism. Targeting less corneal astigmatism theoretically shifts a proportion of the remaining astigmatism to the refractive level. In practice this has been shown to be less than expected when actual post operative manifest refractions are measured and evaluated. The vector planning technique employing asymmetrical corneal astigmatism treatments (FIG. 8) attempts to minimize the non-corneal astigmatism, quantified by ORA, hence gaining the maximum correspondence between corneal and refractive values and potentially improve the optical quality of the perceived image. The best possible equivalence between these two is likely to minimize both lower and higher order optical aberrations within the eye. Referring to FIG. 8, the treatment of irregular astigmatism is effected by applying an optimal asymmetric treatment ($TIA_{SUP\ AB}$ and $TIA_{INF\ AB}$) to each corneal semi-meridian. This maximum correction of astigmatism is denoted as step A to B (AB).

It is envisaged that wavefront measurements are likely in future to make it possible to better match two differing refractive values, one for each semi-meridian, with the two separate topographic values on the cornea, hence employing a separate refractive and topographic measurement for each corneal semi-meridian. This combined treatment paradigm has a greater potential for improving the best corrected vector analysis (BCVA) than using wavefront or topography parameters alone. The ideal ablation shape to effectively correct irregular astigmatism will be determined by an ellipse that has modified dimensions for each semi-meridian. The ellipses may be angularly displaced to achieve the non-orthogonal and asymmetrical treatment requirements.

The treatment changes necessary to address these asymmetrical and non-orthogonal values of the cornea are achieved by creating gradual and undulating variations in contour between the principal meridian of the cornea. Smooth continual rather than rough abrupt changes have a greater prospect for being sustained to combat the natural forces of epithelial healing that over time are likely to smooth out any localised applied unevenness.

The method of vector planning can be expanded upon to refine outcomes in cases of irregular astigmatism. Utilizing asymmetrical vector planning with a separate astigmatism treatment plan for each separate semi-meridian of the cornea would likely result in less overall astigmatism and a more regular corneal profile at the completion of a single corneal surgery correcting sphere and irregular cylinder. Incorporation of these algorithms into future excimer laser technology would potentially improve the outcomes currently achieved by the treatment of spherocylinder in laser vision correction.

Calculation of Treatment for Maximum Reduction of Astigmatism and Regularization of Cornea The first step in the process is the maximum reduction of astigmatism and has been referred to as step A to B (AB) and the second step the regularization of the cornea as step B to C (BC).

Preoperative parameters are displayed in FIG. 7a.
Superior topography 2.60 D@130
Inferior topography 1.90 D@278
Wavefront refraction −3.24 DS/−1.80 DC×18 (BVD=12.5 mm)

The separate semi meridian astigmatic treatments ($TIA_{SUP\ AB}$ and $TIA_{INF\ AB}$) are displayed in FIG. 8 and are calculated based on emphasis of 40% sphericizing the cornea/60% sphericizing the refractive cylinder with an existing ORA of 1.82 D Ax 59 for the superior semi-meridian. The inferior semi-meridian treatment is also based on 40% sphericizing the cornea/60% sphericizing the refractive cylinder applied to an existing ORA of 0.67D Ax 340. Irrespective of the emphasis chosen for the ORA, the maximum amount of astigmatism is being treated in each semi meridian of the cornea.

The vectorial difference between the preoperative topography and the target topography, as determined by the emphasis on neutralizing the ORA, is equal to the astigmatic treatment (TIA) for each semi-meridian. The topography targets (Target $T_{INF\ B}$ and Target $T_{SUP\ B}$) are displayed in FIG. 9.

When the TIA between the two semi-meridians differs, a summation of the TIA's ($TIA_{NET\ AB}$) or average needs to be calculated (FIG. 10) to determine the combined effect on refractive astigmatism. The average of the treatment vectors, the $TIA_{NET\ AB}$, is calculated using a head to tail summation of the $TIA_{SUP\ AB}$ and $TIA_{INF\ AB}$ which is then divided by 2 because there are 2 values involved in the summation calculation:

$$1.87\ D\ Ax\ 29 + 1.71\ D\ Ax\ 194 = 1.73\ D\ Ax\ 22$$

The average treatment vector $TIA_{NET\ AB}$ is added to each of the common pair of refractive values of +1.63 Ax 108 for the 2 semi-meridians (then the axis subsequently is halved to convert to a polar diagram as it would appear on the eye) to obtain a refractive cylinder target ($R_B$) displayed in FIG. 11:

$$1.63\ Ax\ 108 + [+1.73\ Ax\ 22] = +0.25\ Ax\ 53\ (R_B)$$

To regularize the cornea, the topography targets after the first process of the maximum optimized reduction of astigmatism (Target $T_{INF\ B}$ and Target $T_{SUP\ B}$) (step AB) have a second treatment added ($TIA_{SUP\ BC}$ and $TIA_{INF\ BC}$) to target the initial refractive cylinder result (Target $R_B$) of +0.25D Ax 53 (axis 106 on DAVD displayed in FIG. 12).

In this example the resultant topography (Target $T_{INF\ C}$ and Target $T_{SUP\ C}$) and the final refraction (Target $R_C$), which again is calculated by vectorially adding the 2 treatments $TIA_{SUP\ BC}$ and $TIA_{INF\ BC}$, are aligned (FIG. 14) resulting in minimum remaining ORA when Target $R_B$ shifts to Target $R_C$ from the resultant net refractive change.

The remaining ORA i.e. the vectorial difference between the final topography and refractive cylinder targets is at a minimum. The topography targets equal 0.25 D@53 and result from the maximum reduction of astigmatism and regularization and the effect of the second treatments to regularize the cornea ($TIA_{SUP\ BC}$ and $TIA_{INF\ BC}$). These regularization changes of the second process (BC), affect the refractive target (Target $R_B$)→Target $R_C$=0.87 D Ax 53 by shifting an amount equal to the resulting final ORA of 0.62 D Ax 53.

One Step Treatment for Maximum Reduction and Regularization of Irregular Astigmatism (Step A to C)

The treatment required to maximally reduce (AB) and regularize the astigmatism (BC) in one step begins with the 2 preoperative corneal values ($T_{SUP}$ and $T_{INF}$) targeting the refractive target (Target $R_B$) that is calculated from step AB. The single step treatment here ($TIA_{SUP\,AC}$ and $TIA_{INF\,AC}$ in FIG. 15) is the addition of the TIA superior and TIA inferior treatment vectors calculated in step AB (FIG. 9) and step BC (FIG. 12).

Preoperative Parameters

Superior topography 2.60 D@130

Inferior topography 1.90 D@278

Treatment

Superior $TIA_{AC}$=2.82 D Ax 131 (TIA SUP AB+BC)

Inferior $TIA_{AC}$=1.91 D Ax 102 (TIA INF AB+BC)

Targets

Superior topography 0.25 D@53

Inferior topography 0.25 D@233

Refractive target (Target $R_C$)+0.87D Ax 53

Symmetrical And Orthogonal Outcome Is Thus Obtained.

Figure 17:
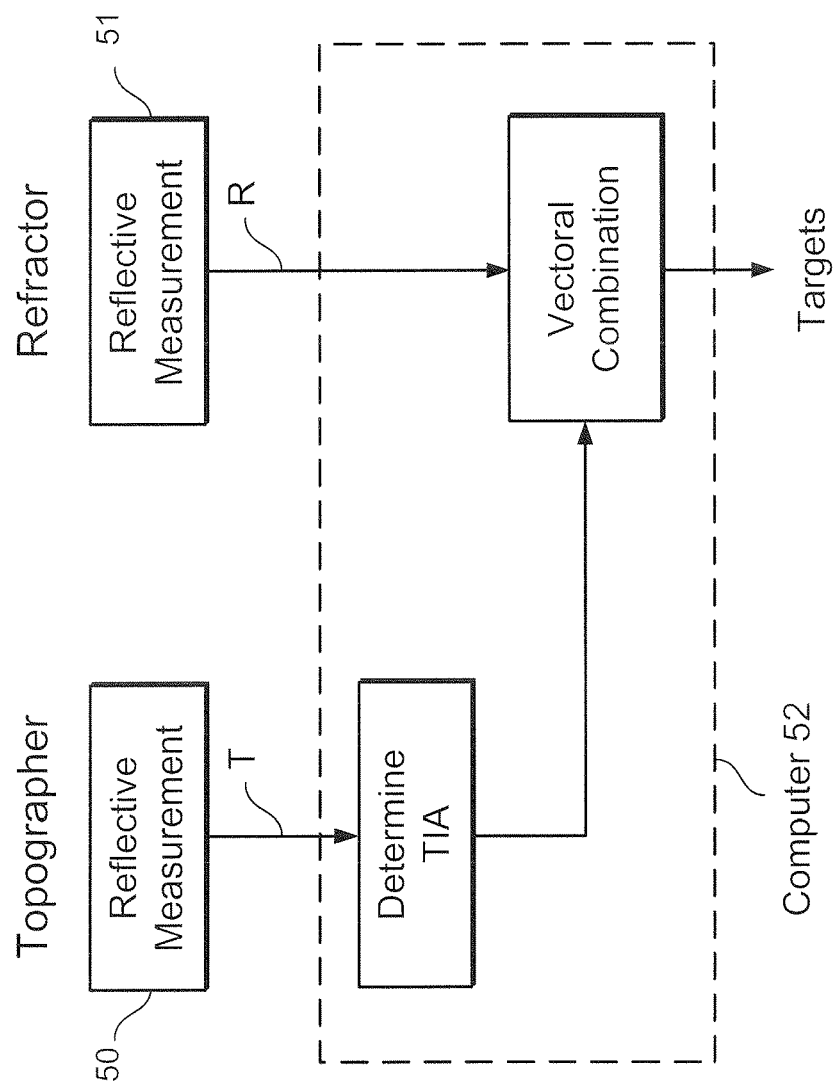
FIG. 17 is a diagrammatic illustration of vector planning apparatus for evaluating and obtaining surgical parameters for treatment of astigmatism in an eye of a patient.

FIG. 17 is a diagrammatic illustration of apparatus for carrying out the methods hereto described.

Therein can be seen a topographer 50 for producing a map of the cornea from which corneal values can be obtained in the 3 mm, 5 mm, and 7 mm zones. FIG. 17 also shows a refractive measuring device which can determine the refractive condition of the eye of a patient. The parameters obtained from the topographer 51 and the refractive measuring device 52 are supplied to computer 53 which carries out the operations heretofore described to produce the topography parameters T sup and T inf as well as TD and CorT and the parameters for TIA sup and TIA inf for the semi-meridians which will provide maximum topographic reduction and minimal ORA.

What is claimed is:

1. Apparatus for reducing and regularizing measured values of astigmatism in an eye of a patient to obtain target values for diagnosis and treatment of the patient, said apparatus comprising:
   a keratometer for measuring the cornea of the eye of the patient to obtain topographic parameters thereof in each semi-meridian of the cornea,
   a device for refractive measurement of the eye to obtain a refractive parameter for both semi-meridians, and
   a computer receiving the topographic and refractive parameters and configured for: (a) reducing the topographic parameters to a minimum value of ORA to obtain maximum treatment to the minimum topographic target parameters T and refractive target R for each semi-meridian, and (b) vectorially combining the topographic parameters T and the refractive parameter R to obtain target induced astigmatism parameters (TIA) which produce said topographic targets T which are regularized, wherein the minimum topographic target parameters T are regularized in one step using the refractive parameter R to obtain the target induced astigmatism parameters (TIA).

2. Apparatus as claimed in claim 1, wherein the computer is configured for:
   receiving measurements from the keratometer and from the device for refractive measurement of corneal and refractive astigmatism values in each of the semi-meridians; and
   determining topographic treatment parameters in each semi-meridian to maximally reduce the topographic astigmatism values in each of the semi-meridians based on minimizing ocular residual astigmatism remaining in each semi-meridian.

3. Apparatus as claimed in claim 2, wherein the computer is configured to vectorially combine said topographic treatment parameters (Target T) for each of the semi-meridians with a common refractive target value R to obtain treatment parameters (TIA) for each semi-meridian in which targets T are regularized.

4. Apparatus as claimed in claim 3, wherein the computer is configured to maximally reduce the determined topographic values T to leave a minimum value of ORA to be neutralised on the cornea.

5. Apparatus as claimed in claim 4, wherein the computer is configured to determine TIA parameters for each semi-meridian by first applying emphasis factors on each topography and refractive parameter to obtain topographic targets T and refractive target R for each semi-meridian, then to obtain an average target T for the two semi-meridians and then vectorially to combine the average value of target T with target R for each semi-meridian.

6. A method for reducing and regularizing measured values of astigmatism in an eye of a patient to obtain target values for diagnosis and treatment of the patient, said method comprising the steps of:
   (a) providing the apparatus of claim 1;
   (b) obtaining with the keratometer parameters representing topography of the eye in superior and inferior semi-meridians of the cornea of the patient,
   (c) obtaining with the device a parameter representing a refractive value for each semi-meridian; and
   (d) supplying the parameters obtained in steps (b) and (c) to the computer and causing the computer (i) to determine topographic treatment parameters in each semi-meridian to maximally reduce topographic astigmatism values in each of the semi-meridians based on minimizing ocular residual astigmatism remaining in each semi-meridian; and (ii) to regularize the thus reduced topographic treatment parameters using a common refractive parameter for the two separate semi-meridians to obtain in one step final treatment target values for the two semi-meridians.

7. Vector planning apparatus for obtaining target parameters for surgical use comprising:
   (i) means for obtaining parameters representing topography of an eye in superior and inferior semi-meridians of the cornea,
   (ii) means for obtaining a parameter representing a refractive value for each semi-meridian, and
   (iii) a computer configured for:
      a) determining a target topographic vector for each semi-meridian from the obtained topography parameters and
      b) vectorially combining said target topographic vector with the refractive value to obtain treatment astigmatism values for the semi-meridians which are equal and regularized, wherein the target topographic vectors determined in (a) are regularized in one step using a common refractive parameter for the respective semi-meridians to obtain the treatment astigmatism values.

8. Apparatus as claimed in claim 7, wherein the computer is configured to obtain a value of ocular residual astigmatism (ORA) by determining the vectorial difference between the corneal and refractive astigmatism values.

9. Apparatus as claimed in claim 7, wherein the computer is configured to reduce the parameters of magnitude in each of said semi-meridians to obtain maximum values of topographic parameters by leaving minimum values of ocular residual astigmatism in each semi-meridian that are equal in magnitude but are asymmetrical, and regularizing the thus obtained values of topography in said semi-meridians to obtain topography parameters which are symmetrical and orthogonal in one step.

10. Apparatus as claimed in claim 9,
    wherein the computer is configured to regularize the symmetrical topographic parameters by vectorially combining each thereof with a common refractive astigmatism value.

11. Apparatus as claimed in claim 10,
    wherein the computer is configured to obtain said common refractive astigmatism value by reducing a measured refractive parameter by reducing said measured vectorial parameter by a proportional amount of said ocular residual astigmatism.

12. A vector planning apparatus for obtaining target parameters for surgical use comprising:
    (i) a keratometer configured to measure the cornea of an eye of a patient and to obtain a plurality of topographic parameters in each of a plurality of zones in each of two semi-meridians of the cornea, wherein the plurality of topographic parameters comprises a plurality of flat and steep keratometric magnitudes with their respective meridians for each of the plurality of zones in each of said semi-meridians; and
    (ii) a computer configured for:
        (a) receiving the plurality of topographic parameters;
        (b) calculating from the plurality of topographic parameters an astigmatism value for each said zone by determining a pair of flat/steep parameters in each said zone having a minimum magnitude of corneal irregularity and determining arithmetic difference between the selected pair in each said zone;
        (c) assigning weighting values to the calculated astigmatism values for the respective zones to obtain weighted values;
        (d) vectorially combining the weighted values to obtain a vector parameter in each of the semi-meridians representing magnitude and axis of topographic irregularity; and
        (e) adding the vector parameters of the semi-meridians to obtain a single topographic value for the entire cornea representing corneal topography astigmatism (CorT).

13. Apparatus as claimed in claim 12, wherein the computer is configured to subtract the vector parameters in the semi-meridians from one another to obtain a topographic parameter representing topographic disparity (TD) between the semi-meridians.

14. Apparatus as claimed in claim 12, wherein each semi-meridian is formed with three concentric, circular zones.

15. Apparatus as claimed in claim 14, wherein the concentric zones in each semi-meridian are at 3 mm, 5 mm and 7 mm.

16. Apparatus as claimed in claim 14, wherein the computer is configured to multiply the parameters of magnitude in each of the respective zones is multiplied by respective weighting factors to produce the weighted values.

17. A method for determining a parameter of magnitude and meridian axis representing corneal astigmatism for use in vector analysis for diagnostic and surgical treatment, comprising the steps of:
    (a) providing the apparatus of claim 12;
    (b) measuring the cornea of an eye of a patient with the keratometer to obtain a plurality of topographic parameters in each of a plurality of zones in each of two semi-meridians of the cornea, wherein the plurality of topographic parameters comprises a plurality of flat and steep keratometric magnitudes with their respective meridians for each of the plurality of zones in each of said semi-meridians; and
    (c) supplying the plurality of parameters obtained in step (b) to the computer and causing the computer to calculate from the plurality of parameters an astigmatism value for each said zone, to assign weighting values to the calculated astigmatism values for the respective zones to obtain weighted values, to vectorially combine the weighted values to obtain a vector parameter in each of the semi-meridians representing magnitude and axis of topographic irregularity; and to calculate from a vector summated mean of the weighted values a single topographic value for the entire cornea representing corneal topography astigmatism (CorT).

\* \* \* \* \*